US008828359B2

(12) United States Patent
Kordikowski et al.

(10) Patent No.: US 8,828,359 B2
(45) Date of Patent: *Sep. 9, 2014

(54) PARTICULATE MATERIALS

(71) Applicants: Andreas Kordikowski, Hellifield (GB); Stephen Ernest Walker, Baildon (GB); Peter York, Ilkley (GB)

(72) Inventors: Andreas Kordikowski, Hellifield (GB); Stephen Ernest Walker, Baildon (GB); Peter York, Ilkley (GB)

(73) Assignee: Nektar Therapeutics, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/908,540

(22) Filed: Jun. 3, 2013

(65) Prior Publication Data

US 2014/0037697 A1 Feb. 6, 2014

Related U.S. Application Data

(63) Continuation of application No. 13/294,881, filed on Nov. 11, 2011, now Pat. No. 8,470,301, which is a continuation of application No. 12/483,378, filed on Jun. 12, 2009, now Pat. No. 8,080,236, which is a continuation of application No. 10/413,457, filed on Apr. 14, 2003, now Pat. No. 7,582,284.

(30) Foreign Application Priority Data

Apr. 17, 2002 (GB) .................................. 0208742.7
Apr. 23, 2002 (GB) .................................. 0209402.7

(51) Int. Cl.
*A61K 9/14* (2006.01)
*A61K 9/12* (2006.01)
*B01J 2/04* (2006.01)
*A61K 9/00* (2006.01)

(52) U.S. Cl.
CPC . *A61K 9/008* (2013.01); *B01J 2/04* (2013.01); *Y10S 514/951* (2013.01)
USPC ............. 424/46; 424/489; 424/499; 424/434; 424/45; 514/951

(58) Field of Classification Search
USPC ............... 424/46, 489, 499, 434, 45; 514/951
See application file for complete search history.

(56) References Cited

U.S. PATENT DOCUMENTS

| | | |
|---|---|---|
| 2,868,691 A | 1/1959 | Porush et al. |
| 2,885,427 A | 5/1959 | Ruh et al. |
| 3,014,844 A | 12/1961 | Thiei et al. |
| 3,219,533 A | 11/1965 | Mullins et al. |
| 3,261,748 A | 7/1966 | Larsen |
| 3,320,125 A | 5/1967 | Grim et al. |
| 3,644,353 A | 2/1972 | Lunts et al. |
| 3,809,294 A | 5/1974 | Torgeson |
| 3,897,779 A | 8/1975 | Hansen |
| 3,994,421 A | 11/1976 | Hansen |
| 4,044,126 A | 8/1977 | Cook et al. |
| 4,129,603 A | 12/1978 | Bell |
| 4,174,295 A | 11/1979 | Bargigia et al. |
| 4,241,048 A | 12/1980 | Durbak et al. |
| 4,294,829 A | 10/1981 | Suzuki et al. |
| 4,311,863 A | 1/1982 | Gumprecht |
| 4,335,121 A | 6/1982 | Phillipps et al. |
| 4,347,236 A | 8/1982 | Tanskanen |
| 4,352,789 A | 10/1982 | Thiel |
| 4,405,598 A | 9/1983 | Brown |
| 4,423,099 A | 12/1983 | Mueller et al. |
| 4,462,983 A | 7/1984 | Azria et al. |
| 4,514,574 A | 4/1985 | Inoue et al. |
| 4,582,731 A | 4/1986 | Smith |
| 4,590,206 A | 5/1986 | Forrester et al. |
| 4,659,696 A | 4/1987 | Hirai et al. |
| 4,670,419 A | 6/1987 | Uda et al. |
| 4,710,495 A | 12/1987 | Bodor |
| 4,737,384 A | 4/1988 | Murthy et al. |
| 4,767,612 A | 8/1988 | Hagen et al. |
| 4,810,488 A | 3/1989 | Jinks |
| 4,814,161 A | 3/1989 | Jinks et al. |

(Continued)

FOREIGN PATENT DOCUMENTS

| | | |
|---|---|---|
| CA | 2075058 A1 | 8/1991 |
| CA | 2062854 A1 | 9/1992 |

(Continued)

OTHER PUBLICATIONS

Japanese Office Action dated Feb. 21, 2013, for Japanese Application No. 2010- 263772.

(Continued)

*Primary Examiner* — Mina Haghighatian
(74) *Attorney, Agent, or Firm* — Patterson & Sheridan, LLP

(57) ABSTRACT

Embodiments of the invention relate to particles of active substances, methods for preparing the particles, formulations containing the particles, and metered dose inhalers containing such particles or formulations. In one embodiment, a composition of an aerosol formulation is provided and contains a particulate active substance of non-micronized, solid particles having a mass median aerodynamic diameter of less than 10 μm suspended in a hydrofluorocarbon fluid vehicle at a concentration within a range from about 0.2% w/v to about 5% w/v. The aerosol formulation exhibits a flocculation volume of about 85% or greater about 1 minute after mixing the particulate active substance and the hydrofluorocarbon fluid vehicle. The particulate active substance contains an alkaloid ergotamine, pharmaceutically acceptable salts thereof, analogs thereof, or derivatives thereof. In some examples, the alkaloid ergotamine contains dihydroergotamine, such as dihydroergotamine mesylate and the hydrofluorocarbon fluid vehicle contains HFA 134a, HFA 227ea, or mixtures thereof.

20 Claims, 7 Drawing Sheets

(56) References Cited

U.S. PATENT DOCUMENTS

Figure 1:
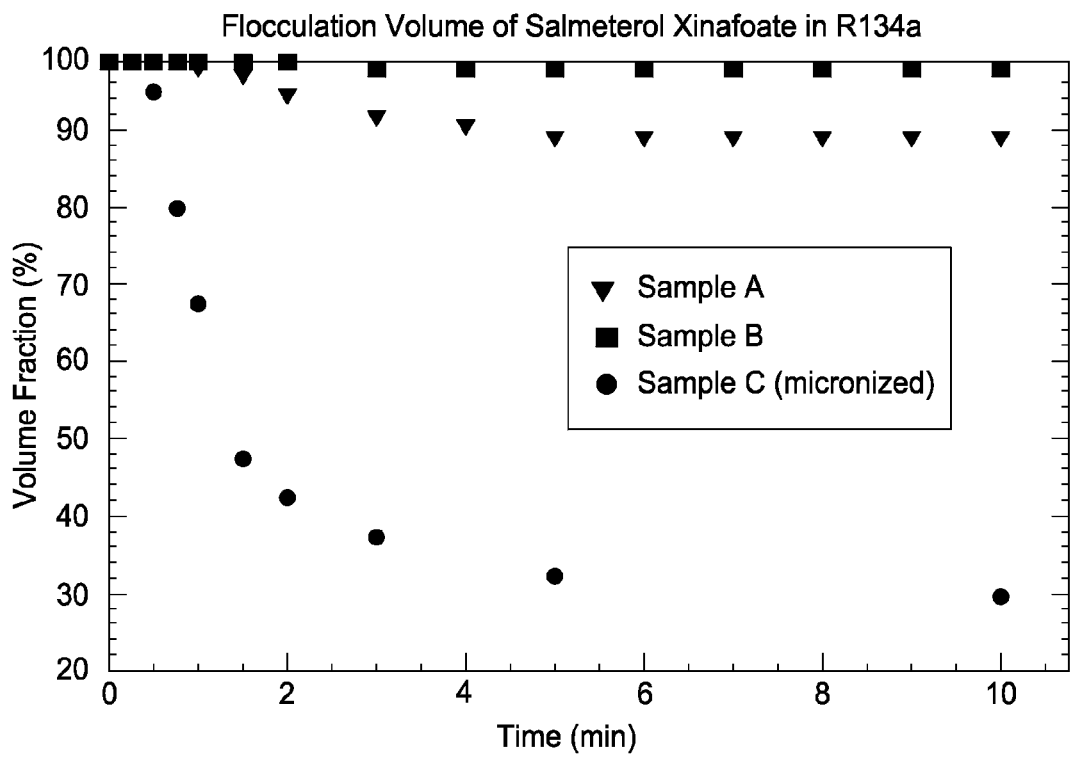

| | | |
|---|---|---|
| 4,851,595 A | 7/1989 | Gumprecht |
| 4,859,696 A | 8/1989 | Kamiya et al. |
| 4,866,051 A | 9/1989 | Hunt et al. |
| 4,884,565 A | 12/1989 | Cocozza |
| 4,923,720 A | 5/1990 | Lee et al. |
| 4,940,171 A | 7/1990 | Gilroy |
| 4,945,119 A | 7/1990 | Smits et al. |
| 4,963,557 A | 10/1990 | Badger et al. |
| 4,970,093 A | 11/1990 | Sievers et al. |
| 5,011,678 A | 4/1991 | Wang et al. |
| 5,043,280 A | 8/1991 | Fischer et al. |
| 5,066,522 A | 11/1991 | Cole et al. |
| 5,106,659 A | 4/1992 | Hastings et al. |
| 5,118,494 A | 6/1992 | Schultz et al. |
| 5,126,123 A | 6/1992 | Johnson |
| 5,130,137 A | 7/1992 | Crowley, Jr. |
| 5,145,684 A | 9/1992 | Liversidge et al. |
| 5,178,878 A | 1/1993 | Wehling et al. |
| 5,182,040 A | 1/1993 | Bartlett et al. |
| 5,182,097 A | 1/1993 | Byron et al. |
| 5,186,164 A | 2/1993 | Raghuprasad |
| 5,190,029 A | 3/1993 | Byron et al. |
| 5,196,575 A | 3/1993 | Sebastian |
| 5,202,110 A | 4/1993 | Dalby et al. |
| 5,206,268 A | 4/1993 | Latter et al. |
| 5,221,731 A | 6/1993 | Weymans et al. |
| 5,223,264 A | 6/1993 | Wehling et al. |
| 5,225,183 A | 7/1993 | Purewal et al. |
| 5,229,486 A | 7/1993 | Paul et al. |
| 5,230,884 A | 7/1993 | Evans et al. |
| 5,232,707 A | 8/1993 | Lokensgard |
| 5,254,330 A | 10/1993 | Ganderton et al. |
| 5,254,755 A | 10/1993 | Li et al. |
| 5,270,305 A | 12/1993 | Palmer |
| 5,290,539 A | 3/1994 | Marecki |
| 5,292,499 A | 3/1994 | Evans et al. |
| 5,302,581 A | 4/1994 | Sarin et al. |
| 5,310,762 A | 5/1994 | Latter et al. |
| 5,314,682 A | 5/1994 | Sweval et al. |
| 5,320,094 A | 6/1994 | Laube et al. |
| 5,320,714 A | 6/1994 | Brendel |
| 5,331,953 A | 7/1994 | Andersson et al. |
| 5,348,730 A | 9/1994 | Greenleaf et al. |
| 5,354,934 A | 10/1994 | Pitt et al. |
| 5,364,838 A | 11/1994 | Rubsamen |
| 5,376,359 A | 12/1994 | Johnson |
| 5,376,386 A | 12/1994 | Ganderton et al. |
| 5,384,133 A | 1/1995 | Boyes et al. |
| 5,424,076 A | 6/1995 | Gorissen et al. |
| 5,427,282 A | 6/1995 | Greenleaf et al. |
| 5,437,798 A | 8/1995 | LaRoche et al. |
| 5,439,670 A | 8/1995 | Purewal et al. |
| 5,458,135 A | 10/1995 | Patton et al. |
| 5,464,632 A | 11/1995 | Cousin et al. |
| 5,474,759 A | 12/1995 | Fassberg et al. |
| 5,492,688 A | 2/1996 | Byron et al. |
| 5,508,023 A | 4/1996 | Byron et al. |
| 5,518,998 A | 5/1996 | Backstrom et al. |
| 5,548,004 A | 8/1996 | Mandel et al. |
| 5,560,543 A | 10/1996 | Smith et al. |
| 5,605,674 A | 2/1997 | Purewal et al. |
| 5,607,697 A | 3/1997 | Alkire et al. |
| 5,620,631 A | 4/1997 | Heiskel et al. |
| 5,639,441 A | 6/1997 | Sievers et al. |
| 5,639,475 A | 6/1997 | Bettman et al. |
| 5,653,962 A | 8/1997 | Akehurst et al. |
| 5,658,549 A | 8/1997 | Akehurst et al. |
| 5,674,471 A | 10/1997 | Akehurst et al. |
| 5,674,472 A | 10/1997 | Akehurst et al. |
| 5,674,473 A | 10/1997 | Purewal et al. |
| 5,676,929 A | 10/1997 | Akehurst et al. |
| 5,681,545 A | 10/1997 | Purewal et al. |
| 5,683,676 A | 11/1997 | Akehurst et al. |
| 5,683,677 A | 11/1997 | Purewal et al. |
| 5,688,782 A | 11/1997 | Neale et al. |
| 5,695,743 A | 12/1997 | Purewal et al. |
| 5,707,634 A | 1/1998 | Schmitt |
| 5,708,039 A | 1/1998 | Daly et al. |
| 5,709,886 A | 1/1998 | Bettman et al. |
| 5,720,940 A | 2/1998 | Purewal et al. |
| 5,725,836 A | 3/1998 | Rouanet et al. |
| 5,736,124 A | 4/1998 | Akehurst et al. |
| 5,744,123 A | 4/1998 | Akehurst et al. |
| 5,766,573 A | 6/1998 | Purewal et al. |
| 5,770,559 A | 6/1998 | Manning et al. |
| 5,776,432 A | 7/1998 | Schultz et al. |
| 5,776,434 A | 7/1998 | Purewal et al. |
| 5,776,491 A | 7/1998 | Allen, Jr. et al. |
| 5,795,594 A | 8/1998 | York et al. |
| 5,807,576 A | 9/1998 | Allen, Jr. et al. |
| 5,807,578 A | 9/1998 | Acosta-Cuello et al. |
| 5,817,293 A | 10/1998 | Akehurst et al. |
| 5,833,950 A | 11/1998 | Taylor et al. |
| 5,851,453 A | 12/1998 | Hanna et al. |
| 5,874,029 A | 2/1999 | Subramaniam et al. |
| 5,874,064 A | 2/1999 | Edwards et al. |
| 5,916,540 A | 6/1999 | Akehurst et al. |
| 5,919,435 A | 7/1999 | Taylor et al. |
| 5,922,306 A | 7/1999 | Akehurst et al. |
| 5,922,355 A | 7/1999 | Parikh et al. |
| 5,922,675 A | 7/1999 | Baker et al. |
| 5,997,848 A | 12/1999 | Patton et al. |
| 6,006,745 A | 12/1999 | Marecki |
| 6,013,245 A | 1/2000 | Taylor et al. |
| 6,024,981 A | 2/2000 | Khankari et al. |
| 6,030,682 A | 2/2000 | Marecki |
| 6,054,488 A | 4/2000 | Oliver et al. |
| 6,063,138 A | 5/2000 | Hanna et al. |
| 6,063,910 A | 5/2000 | Debenedetti et al. |
| 6,068,832 A | 5/2000 | Berry et al. |
| 6,117,455 A | 9/2000 | Takada et al. |
| 6,123,924 A | 9/2000 | Mistry et al. |
| 6,136,295 A | 10/2000 | Edwards et al. |
| 6,149,941 A | 11/2000 | Schwarz et al. |
| 6,153,173 A | 11/2000 | Sapsford et al. |
| 6,156,339 A | 12/2000 | Grother et al. |
| 6,200,549 B1 | 3/2001 | Akehurst et al. |
| 6,221,339 B1 | 4/2001 | Akehurst et al. |
| 6,238,647 B1 | 5/2001 | Akehurst et al. |
| 6,251,368 B1 | 6/2001 | Akehurst et al. |
| 6,290,991 B1 | 9/2001 | Roser et al. |
| 6,303,103 B1 | 10/2001 | Akehurst et al. |
| 6,306,368 B1 | 10/2001 | Taylor et al. |
| 6,306,369 B1 | 10/2001 | Akehurst et al. |
| 6,309,623 B1 | 10/2001 | Weers et al. |
| 6,309,624 B1 | 10/2001 | Sapsford et al. |
| 6,316,029 B1 | 11/2001 | Jain et al. |
| 6,331,310 B1 | 12/2001 | Roser et al. |
| 6,333,023 B1 | 12/2001 | Akehurst et al. |
| 6,346,323 B1 | 2/2002 | Nettesheim |
| 6,352,684 B1 | 3/2002 | Purewal et al. |
| 6,413,497 B1 | 7/2002 | Weil et al. |
| 6,416,743 B1 | 7/2002 | Fassberg et al. |
| 6,419,899 B1 | 7/2002 | Weil et al. |
| 6,440,337 B1 | 8/2002 | Hanna et al. |
| 6,503,480 B1 | 1/2003 | Edwards et al. |
| 6,503,482 B1 | 1/2003 | Fassberg et al. |
| 6,558,651 B1 | 5/2003 | Riebe et al. |
| 6,656,453 B2 | 12/2003 | Riebe et al. |
| 6,656,492 B2 | 12/2003 | Kajiyama et al. |
| 6,743,413 B1 | 6/2004 | Schultz et al. |
| 6,860,907 B1 | 3/2005 | Hanna et al. |
| 6,884,408 B2 | 4/2005 | Rabinowitz et al. |
| 7,582,284 B2 * | 9/2009 | Kordikowski et al. ......... 424/46 |
| 7,829,123 B2 | 11/2010 | Sundholm et al. |
| 8,080,236 B2 * | 12/2011 | Kordikowski et al. ......... 424/46 |
| 8,470,301 B2 * | 6/2013 | Kordikowski et al. ......... 424/46 |
| 2002/0000681 A1 | 1/2002 | Gupta et al. |
| 2002/0071812 A1 | 6/2002 | Weil et al. |
| 2002/0081266 A1 | 6/2002 | Woolfe et al. |
| 2002/0114844 A1 | 8/2002 | Hanna et al. |
| 2003/0047824 A1 | 3/2003 | Hanna et al. |
| 2003/0086970 A1 | 5/2003 | Woolfe et al. |
| 2003/0109421 A1 | 6/2003 | Palakodaty et al. |

(56) References Cited

U.S. PATENT DOCUMENTS

| | | |
|---|---|---|
| 2003/0170310 A1 | 9/2003 | Wadhwa |
| 2003/0175214 A1 | 9/2003 | Staniforth et al. |
| 2004/0058007 A1 | 3/2004 | Sundholm et al. |
| 2004/0071783 A1 | 4/2004 | Hanna et al. |
| 2004/0119179 A1 | 6/2004 | Perrut et al. |
| 2004/0197273 A1 | 10/2004 | Schultz et al. |
| 2005/0170000 A1 | 8/2005 | Walker et al. |
| 2005/0206023 A1 | 9/2005 | Hanna et al. |
| 2007/0009604 A1 | 1/2007 | Sundholm et al. |

FOREIGN PATENT DOCUMENTS

| | | |
|---|---|---|
| DE | 2703119 A1 | 8/1977 |
| DE | 2737132 A1 | 2/1978 |
| DE | 3018550 A1 | 12/1980 |
| DE | 4041563 A1 | 6/1992 |
| DK | 134923 | 7/1997 |
| EP | 0039369 A1 | 11/1981 |
| EP | 0072046 A1 | 2/1983 |
| EP | 0172672 A1 | 2/1986 |
| EP | 0322687 A2 | 7/1989 |
| EP | 0365119 A2 | 4/1990 |
| EP | 0372777 A2 | 6/1990 |
| EP | 0379793 A1 | 8/1990 |
| EP | 0384371 A1 | 8/1990 |
| EP | 0403301 A2 | 12/1990 |
| EP | 455892 A1 | 11/1991 |
| EP | 0461930 A1 | 12/1991 |
| EP | 0464171 A1 | 1/1992 |
| EP | 469725 A1 | 2/1992 |
| EP | 0504112 A2 | 9/1992 |
| EP | 512693 A1 | 11/1992 |
| EP | 0518600 A1 | 12/1992 |
| EP | 0518601 A1 | 12/1992 |
| EP | 0542314 A1 | 5/1993 |
| EP | 628331 A1 | 12/1994 |
| EP | 0655237 A1 | 5/1995 |
| EP | 0656206 A1 | 6/1995 |
| EP | 0656207 A1 | 6/1995 |
| EP | 0661091 A1 | 7/1995 |
| EP | 674541 A1 | 10/1995 |
| EP | 0677332 A2 | 10/1995 |
| EP | 681843 A2 | 11/1995 |
| EP | 709085 A1 | 5/1996 |
| EP | 1004349 A1 | 5/2000 |
| EP | 1022020 A2 | 7/2000 |
| EP | 1092430 A1 | 4/2001 |
| GB | 837465 A | 6/1960 |
| GB | 1429184 A | 3/1976 |
| GB | 2001334 A | 1/1979 |
| GB | 2076422 A | 12/1981 |
| GB | 2105189 A | 3/1983 |
| GB | 2235627 A | 3/1991 |
| GB | 2322326 A | 8/1998 |
| GB | 2371501 A | 7/2002 |
| GB | 03003381 | 1/2003 |
| GB | 03003399 | 1/2003 |
| JP | 60227805 A | 11/1985 |
| JP | 1176437 A | 7/1989 |
| JP | 5280282 A | 10/1993 |
| JP | 2001-502350 | 2/2001 |
| SE | 437766 B | 3/1985 |
| WO | WO-8102975 A1 | 10/1981 |
| WO | WO-8603750 A1 | 7/1986 |
| WO | WO-8604233 A1 | 7/1986 |
| WO | WO-9003782 A2 | 4/1990 |
| WO | WO-9007333 A1 | 7/1990 |
| WO | WO-9009780 A1 | 9/1990 |
| WO | WO-9011754 A1 | 10/1990 |
| WO | WO-9102545 A1 | 3/1991 |
| WO | WO-9104011 A1 | 4/1991 |
| WO | WO-9111173 A1 | 8/1991 |
| WO | WO-9111495 A1 | 8/1991 |
| WO | WO-9111496 A1 | 8/1991 |
| WO | WO-9114422 A1 | 10/1991 |
| WO | WO-9200061 A1 | 1/1992 |
| WO | WO-9200062 A1 | 1/1992 |
| WO | WO-9200107 A1 | 1/1992 |
| WO | WO-9206675 A1 | 4/1992 |
| WO | WO-9208446 A1 | 5/1992 |
| WO | WO-9208447 A1 | 5/1992 |
| WO | WO-9211190 A2 | 7/1992 |
| WO | WO-9222286 A1 | 12/1992 |
| WO | WO-9222287 A1 | 12/1992 |
| WO | WO-9222288 A1 | 12/1992 |
| WO | WO-9305765 A1 | 4/1993 |
| WO | WO-9311743 A1 | 6/1993 |
| WO | WO-9311744 A1 | 6/1993 |
| WO | WO-9311745 A1 | 6/1993 |
| WO | WO-9311747 A1 | 6/1993 |
| WO | WO-9403153 A1 | 2/1994 |
| WO | WO-9407514 A1 | 4/1994 |
| WO | WO-9500127 A1 | 1/1995 |
| WO | WO-9501221 | 1/1995 |
| WO | WO-9501324 A1 | 1/1995 |
| WO | WO-9521688 A1 | 8/1995 |
| WO | WO-9531479 A1 | 11/1995 |
| WO | WO-9600610 A1 | 1/1996 |
| WO | WO-9714407 A1 | 4/1997 |
| WO | WO-9731691 A1 | 9/1997 |
| WO | WO-9736574 A1 | 10/1997 |
| WO | WO-9813136 A1 | 4/1998 |
| WO | WO-9814179 A1 | 4/1998 |
| WO | WO-9817676 A1 | 4/1998 |
| WO | WO-9836825 | 8/1998 |
| WO | WO-9846215 A1 | 10/1998 |
| WO | WO-9852542 A1 | 11/1998 |
| WO | WO-9852544 A1 | 11/1998 |
| WO | WO-9917742 A2 | 4/1999 |
| WO | WO-9944733 A1 | 9/1999 |
| WO | WO-9952507 A1 | 10/1999 |
| WO | WO-9952550 A1 | 10/1999 |
| WO | WO-9955319 A1 | 11/1999 |
| WO | WO-9959710 A1 | 11/1999 |
| WO | WO-9964014 A1 | 12/1999 |
| WO | WO-9966903 A2 | 12/1999 |
| WO | WO-0030612 A1 | 6/2000 |
| WO | WO-0030613 A1 | 6/2000 |
| WO | WO-0030617 A1 | 6/2000 |
| WO | WO-0067892 A1 | 11/2000 |
| WO | WO-0103821 A1 | 1/2001 |
| WO | WO-02058674 A1 | 1/2001 |
| WO | WO-0115664 A2 | 3/2001 |
| WO | WO-0187278 A1 | 11/2001 |
| WO | WO-0206675 A2 | 1/2002 |
| WO | WO-0208447 A2 | 1/2002 |
| WO | WO-0232462 A1 | 4/2002 |
| WO | WO-0238127 A2 | 5/2002 |
| WO | WO-02078675 | 10/2002 |
| WO | WO-03008082 A1 | 1/2003 |
| WO | WO-03070225 A1 | 8/2003 |
| WO | WO-03074029 A1 | 9/2003 |
| WO | WO-2004098561 A2 | 11/2004 |

OTHER PUBLICATIONS

Al-Omran et al., "Formulation and Physicochemical Evaluations of Diclofenac Sodium Chewable Tablets", Saudi Pharmaceutical J., 10(4):177-183, (2002).

Barj et al. "Submicronic MgAl2O4 Powder Synthesis in Supercritical Ethanol." J. of Materials Sci. vol. 27. No. 8 p. 2187-2192 (1992).

Bleich et al. "Aerosol Solvent Extraction System—A New Microparricle Production Technique." International J. of Pharmaceutics. vol. 97. n. 111-117 (1993).

Bodmeier et al., "Polymeric Microspheres Prepared by Spraying Into Compressed Carbon Dioxide." Pharmaceutical Research. vol. 12. No. 8, 0.1211-1217 (1995).

Chang et al , "Separation of B-Carotene Mixtures Precipitated from Liquid Solvents with High-Pressure C02." Biotechnol. Prog .o No. 7. 0.275-278 (1991).

(56) References Cited

OTHER PUBLICATIONS

Chen et al. "Supercritical antisolvent fractionation of polyethylene simulated with multistage algorithm and SAFT equation of state: staging leads to high selectivity enhancements for light fractions." Ind. Ene:. Chem Res .o vol. 33. p. 306-310 (1994).

Chhor et al .o "Synthesis of Submicron TIO2 Powders in Vapor. Liquid and Supercritical Phases. a Comparative Study," Materials Chemistry and Physics. vol. 32. n. 249-254 (1992).

Colthorpe P. et al., "The pharmacokinetics of pulmonary-delivered insulin: a comparison of intratracheal and aerosol administration to the rabbit.," Pharmaceutical Research. 1992. vol. 9. No. 6, pp. 764-768.

Cygnarowicz et al., "Design and Control of a Process to Extract B-Carotene with Supercritical Carbon Dioxide." Biotechnol. Prog:. vol. 6. o. 82-91 (1990).

Debenedetii et al., "Supercritical Fluids : A New Medium for the Formation of Particles of Biomedical Interest." Proceed. Intern. Svrno. Control Rel. Bioact. Mater. 20, p. 141-142 (1993).

Debenedetti et al., "Application of Supercritical Fluids for the Production of Sustained Delivery Devices." J. Cont. Rel. No. 24. p. 27-44 (1993).

Debenedetti et al., "Rapid Expansion of Supercritical Solutions (RESS): Fundamentals and Applications." Fluid Phase Equilibria. vol. 82. o. 311-321 (1993).

Dixon et al .o "Polymeric Materials Formed by Precipitation with a Compressed Fluid Antisolvent." AIChE J . . . vol. 39 (No. O. p. 127-139 (1993).

Donsi et al., "Micronization by Means of Supercritical Fluids: Possibility of Application to Pharmaceutical Field," Pharm. ACTA BEL V. 66, Nr. 5-6. p. 170-173 (1991).

Elliott, et: al . "Parenteral Absorption of Insulin From the Lung in Diabetic Children." .Aust:. Paediatr. J. 1987, vol. 23. pp. 293-297.

Francis. "Ternary Systems of Liquid Carbon Dioxide," J. of Physical Chemistry. vol. 58. D. 1099-1114 (1954).

Gallagher et al., "Gas Anti-Solvent Recrystallization of RDX: Formation of Ultra-fine Particles of a Difficult-to-Comminute Exolosive." J. of Supercritical Fluids. No. 5, o. 130-142 (1992).

Gallagher et al., "Gas AntiSolvent Recrystallization: New Process to Recrystallize Compounds Insoluble in Supercritical Fluids," ACS Symp. Ser No. 406. p. 334-354 (1989).

Ghaderi et al., "A New Method for Preparing Biodegradable Microparticles and Entrapment of Hydrocortisone in DL-PLG Microparticles Using Supercritical Fluids," European J. of Pharm. Sci . . . vol. 10. No. 1. Mar. 2000. D. 1-9.

J. D. Meyer et al. "Preparation and in vitro characterization of gentamycin-impregnated biodegradable beads suitable for treatment of osteomyelitis." J. of Pharm. Sci. vol. 87. No. 9, Sep. 1, 1998. p. 1149-1154.

Jung et al .o "Particle Design Using Supercritical Fluids: Literature and Patent Survev." J. of Supercritical Fluids vol. 20. n. 179-219 (2001).

Lahiere et al., "Mass-Transfer Efficiencies of Column Contactors in Supercritical Extraction Service." Ind. Ene:. Chern. Res. No. 26. p. 2086-2092 (1987).

Larson et al .o "Evaluation of Supercritical Fluid Extraction in the Pharmaceutical Industry." Biotech. Progress. vol. 2 (No. 2). p. 73-82 (1986).

Lee, Shih-Wei et al., "Development of an aerosol dosage form containing insulin," Journal of Pharmaceutical Sciences. vol. 65, No. 4, Apr. 1976, pp. 567-572.

Loth et al., "Properites and Dissolution of Drugs Micronized by Crystallization from Supercritical Gases." International J. of Pharmaceuticals. vol. 32. o. 265-267 (1986).

Matson et al., "Production of Powders and Films by the Rapid Expansion of Supercritical Solutions." J. of Materials Science. No. 22. 0.1919-1928 (1987).

Mohamed et al.. "Solids Formation After the Expansion of Supercritical Mixtures." Supercritical Fluid Science and Technology. Chapter 23. American Chemical Society, p. 355-378 ( 1989).

Nagai, Tsuneji et al., "Powder Dosage Form of Insulin for Nasal Administration," Journal of Controlled Release. 1984. vol. 1, pp. 15-22.

Phillips et al, "Rapid Expansion from Supercritical Solutions: Application to Pharmaceutical Processes," International J. of Pharmaceutics, vol. 94, p. 1-10 (1993).

Randolph et al., "Sub-micrometer-sized biodegradable particles of poly(L-lactic acid) via the gas antisolvent spray precipitation process," Biotechnol. Prog, vol. 9, No. 4, o. 429-435 (1993).

Stahl et al, "Dense Gas Extraction on a Laboratory Scale: A Survey of some Recent Results", Fluid Phase Equilibria, 10, p. 269, 1983).

Steckel et al., "Metered-dose inhaler formulation of fluticasone-17-propionate micronized with supercritical carbon dioxide using the alternative propellant HFA-227", International J. of Pharmaceutics, 173 (1998), pp. 25-33.

Tom & Debenedetti, "Particle Formation with Supercritical Fluids—A Review", J. Aerosol. Sci., 22(5):555-584, (1991).

Tom et al., "Applications of Supercritical Fluids in the Controlled Release of Drugs," ACS Symposium Series, Supercritical Fluid Engineering Science Fundamentals and Applications, Chpl. 19. p. 238-257 (1993).

Tom et al., "Formation of Bioerodible Polymeric Microspheres and Microparticles by Rapid Expansion of Supercritical Solutions," Biotechnol. Prog., vol. 7, p. 403-411 (1991).

Yeo et al., Formation of Microparticulate Protein Powders Using a Supercritical Fluid Antisolvent, Biotechnology and Bioengineering, vol. 41, p. 341-346 (1993).

* cited by examiner

PARTICULATE MATERIALS

CROSS-REFERENCE TO RELATED APPLICATIONS

This application is a continuation of U.S. Ser. No. 13/294,881, filed Nov. 11, 2011, which is a continuation of U.S. Ser. No. 12/483,378, filed Jun. 12, 2009, now U.S. Pat. No. 8,080,236, which is a continuation of U.S. Ser. No. 10/413,457, filed Apr. 14, 2003, now U.S. Pat. No. 7,582,284, which claims priority to GB 0208742.7, filed Apr. 17, 2002, and to GB 0209402.7, filed Apr. 23, 2002, which U.S. applications are herein incorporated by reference in their entirety.

FIELD OF THE INVENTION

Embodiments of the invention relate to particles of active substances, methods for preparing the particles, formulations containing the particles, and metered dose inhalers containing the particles or formulations.

BACKGROUND TO THE INVENTION

Certain pharmaceuticals may be delivered to the nose and/or lungs of a patient by inhalation, using an inhaler device of which there are several known types. In some of these devices, the drug (or a formulation containing the drug, for instance together with a pharmaceutically acceptable excipient such as lactose) is suspended in particulate form in a fluid vehicle, which acts to transport the drug in a suitably disperse state towards the intended site of administration. The vehicle may be a pressurized propellant fluid if the drug is to be delivered in aerosolized form. "Metered dose inhalers" (MDIs) may for example be used to effect such delivery, for instance those used to dispense budesonide (Pulmicort™ AstraZeneca), salbutamol (Ventolin™ Glaxo SmithKline and Proventil™ HFA, Schering Plough), salmeterol xinafoate (Serevent™, Glaxo SmithKline) and fluticasone (Flovent™ Glaxo SmithKline).

Typical propellant fluids include hydrofluoroalkanes such as 1,1,1,2-tetrafluoroethane (available as HFA 134a), 1,1,1,2,3,3,3-heptafluoropropane (available as HFA 227ea) and 1,1,2,2,3-pentafluoropropane.

The particulate drug must be suspended as uniformly as possible in the fluid vehicle. This is usually achieved by shaking the inhalation device prior to dispensing a dose of the drug. It is clearly desirable that the drug remains suspended in the vehicle for a sufficient length of time after shaking to allow it to reach the intended site of administration. However, particulate drug/propellant suspensions tend only to be stable for limited periods of time. Where the drug is denser than the propellant, the tendency is for it to "settle" or "flocculate", i.e., to fall out of suspension. Where it is less dense than the propellant, the drug tends to "cream" or float towards the top of the propellant volume. This can reduce the efficiency and therefore also accuracy of drug dosage delivery. Often dispersion enhancing agents such as surfactants need to be added to the drug/propellant mixture to achieve and sustain a suitably uniform suspension.

Even using such techniques, it has typically proved difficult to prepare inhalable suspensions which are stable during normal storage periods and conditions and which give uniform dosing throughout the useful life of the average inhaler.

It has also been proposed to use hollow, or at least partially fluid containing, particles in MDI formulations in order to obtain improved dispersibility—see for instance the perforated microstructures described in U.S. Pat. No. 6,309,623 and the hollow microspheres disclosed in WO-97/36574, both suggested for use in inhalers.

Particulate active substances, such as drugs, may be produced by a variety of known methods, including for example crystallization from solution, anti-solvent precipitation from solution, milling, micronization, spray drying, freeze drying or combinations of such processes. Also known are particle formation processes which make use of supercritical or near-critical fluids, either as solvents for the substance of interest—as in the process known as RESS (Rapid Expansion of Supercritical Solution—see Tom & Debenedetti, J. Aerosol. Sci., 22 (5), 555-584 (1991))—or as anti-solvents to cause the substance to precipitate from another solution—as in the process known as GAS (Gas Anti-Solvent) precipitation (see Gallagher et al., ACS Symp. Ser., 406, p. 334 (1989)).

In general, however, known processes for producing inhalable drugs yield particles which perform poorly in propellant fluids, i.e., they exhibit poor flocculation behavior. For many known particulate drugs, the tendency to flocculate can be a severe problem, with significant settling occurring within less than a minute of shaking the suspension and thus often before a dose of the drug has been successfully dispensed or at least before it has reached its target site of administration.

It would therefore be desirable to provide particulate drugs, and indeed other active substances which may need to be delivered in suspension in fluid vehicles, which have improved flocculation behavior in such vehicles.

SUMMARY OF THE INVENTION

According to a first aspect of the present invention there is provided an active substance in particulate form, which is insoluble in the fluid vehicle 1,1,1,2-tetrafluoroethane (HFA 134a) and which when suspended in that vehicle, at a concentration of from 0.2 to 5% w/v, exhibits a flocculation volume of 35% or greater after 5 minutes.

According to a second aspect, the invention provides an active substance in particulate form, which is insoluble in the fluid vehicle 1,1,1,2,3,3,3-heptafluoropropane (HFA 227ea) and which when suspended in that vehicle, at a concentration of from 0.2 to 5% w/v, exhibits a flocculation volume of 35% or greater after 5 minutes.

A third aspect of the present invention provides an active substance in particulate form, which is insoluble in the fluid vehicle 1,1,1,2-tetrafluoroethane (HFA 134a) and which when suspended in that vehicle at a concentration of from 0.2 to 5% w/v exhibits a flocculation volume after 5 minutes which is at least 20% higher, preferably at least 50% or 150% or 200% or 250% higher, than that exhibited by the same chemical entity having the same or a similar particle size (typically measured MMAD, "similar" here meaning within 80 to 120%, preferably within 90 to 110%, of the measured MMAD) but prepared using a micronization process.

A fourth aspect provides an active substance in particulate form, which is insoluble in the fluid vehicle 1,1,1,2,3,3,3-heptafluoropropane (HFA 227ea) and which when suspended in that vehicle at a concentration of from 0.2 to 5% w/v exhibits a flocculation volume after 5 minutes which is at least 20% higher, preferably at least 50% or 150% or 200% or 250% higher, than that exhibited by the same chemical entity having the same or a similar particle size (as described above) but prepared using a micronization process.

A fifth aspect of the present invention provides an active substance in particulate form, which is insoluble in the fluid vehicle 1,1,1,2-tetrafluoroethane (HFA 134a) and which when suspended in that vehicle at a concentration of from 0.2 to 5% w/v exhibits a rate of change (decrease) in flocculation volume, during the first 60 seconds after thorough mixing of the active substance and vehicle, of 20% per minute or less.

A sixth aspect provides an active substance in particulate form, which is insoluble in the fluid vehicle 1,1,1,2,3,3,3-heptafluoropropane (HFA 227ea) and which when suspended in that vehicle at a concentration of from 0.2 to 5% w/v exhibits a rate of change (decrease) in flocculation volume, during the first 60 seconds after thorough mixing of the active substance and vehicle, of 20% per minute or less.

A seventh aspect of the present invention provides the use of a supercritical fluid processing method to produce an active substance in particulate form, for the purpose of improving the flocculation performance of the substance.

According to an eighth aspect of the present invention, there is provided an active substance for use in a method of surgery, therapy or diagnosis practiced on a human or animal body, in which method the substance is delivered to a patient in suspension in a nonsolvent fluid vehicle in which the flocculation performance of the substance is as defined above in relation to any one of the first to the sixth aspects of the invention.

A ninth aspect of the invention provides the use of an active substance in the manufacture of a medicament which comprises a suspension of that substance in a nonsolvent fluid vehicle, in which suspension the flocculation performance of the active substance is as defined above in relation to any one of the first to the sixth aspects of the invention. The medicament may be for use in a method of surgery, therapy or diagnosis practiced on a human or animal body, and is preferably suitable for delivery by inhalation.

A tenth aspect provides the use of an active substance according to any one of the first to the sixth aspects, in suspension in a nonsolvent fluid vehicle at a concentration of at least 0.2% w/v, preferably at least 0.5% w/v, and more preferably the suspension containing no, or less than 0.1% w/w based on the weight of the active substance, preferably less than 0.01% w/w or less than 0.001 or 0.0001% w/w, dispersion enhancing or stabilizing additives such as surfactants. The suspension preferably contains no co-solvents or lubricity enhancing additives.

An eleventh aspect of the invention provides a formulation, typically an aerosol formulation, containing an active substance according to any one of the first to the sixth aspects suspended in a nonsolvent fluid vehicle. Aerosol formulations according to this aspect typically comprise a fine particle fraction of at least 25%, preferably at least 30%, most preferably at least 35%.

A twelfth aspect of the present invention provides a drug delivery device, preferably an inhaler, which contains one or more dosage formulations of an active substance according to any one of the first to the sixth aspects, and preferably also a suitable fluid vehicle in which to aerosolize the substance. Alternatively, the delivery device may contain, or be able to produce, one or more aerosol formulations according to the eleventh aspect of the invention. The delivery device is preferably of the type designed to deliver a predetermined dose of an active substance in a pressurized fluid vehicle, for instance a metered dose inhaler (which term includes pressurized metered dose inhalers (pMDIs)).

A thirteenth aspect of the invention provides an aerosol can containing an aerosol formulation according to the eleventh aspect of the invention, and which is suitable for use in a delivery device such as a MDI, preferably a device according to the twelfth aspect of the invention.

According to a fourteenth aspect, the invention provides a method for delivering an active substance, the method involving charging an aerosol can with an active substance and/or a formulation according to the invention. Subsequent delivery of the can contents may be via a delivery device such as a MDI.

A fifteenth aspect provides a method of treatment of a human or animal patient, which method involves administering to the patient, preferably using a method according to the fourteenth aspect of the invention, an active substance and/or a formulation according to the invention.

These and other aspects of the invention will be readily apparent in view of the detailed discussion and examples below.

BRIEF DESCRIPTION OF THE DRAWINGS

FIG. 1 depicts the time variation in flocculation volume of three samples made according to the present invention in HFA 134a, expressed as a percentage of the initial volume.

FIG. 2 depicts the time variation in flocculation volume of three samples made according to the present invention in HFA 227ea, expressed as a percentage of the initial volume.

FIG. 3 depicts the time variation in flocculation volume of budesonide samples made according to the present invention in HFA 134a, expressed as a percentage of the initial volume.

FIG. 4 depicts the time variation in flocculation volume of budesonide samples made according to the present invention in HFA 227ea, expressed as a percentage of the initial volume.

FIG. 5 is a plot depicting the changes in flocculation volume of particulates in HFA 134a made according to the invention over a 10 minute period, expressed as a percentage of the initial volume.

FIG. 6 is a plot depicting the changes in flocculation volume of particulates in HFA 227ea made according to the invention over a 10 minute period, expressed as a percentage of the initial volume.

FIG. 7 is a plot depicting the changes in flocculation volume of particulates in HFA 134a made according to the invention over a 10 minute period, expressed as a percentage of the initial volume.

FIG. 8 is a plot depicting the changes in flocculation volume of particulates in HFA 227ea made according to the invention over a 10 minute period, expressed as a percentage of the initial volume.

FIG. 9 is a plot depicting the changes in flocculation volume of DHE particulates in HFA 227ea made according to the invention.

FIG. 10 is a plot depicting the changes in flocculation volume of particulates in HFA 134a made according to the invention.

FIG. 11 is a plot depicting the changes in flocculation volume of particulates in HFA 227ea made according to the invention.

FIG. 12 is a plot depicting the changes in flocculation volume of particulates in HFA 134a made according to the invention.

FIG. 13 is a plot depicting the changes in flocculation volume of particulates in HFA 227ea made according to the invention.

DETAILED DESCRIPTION

Flocculation volume, as referred to herein, is a measure of the amount of the vehicle which is occupied by the particulate suspension; a higher value therefore indicates less flocculation (in the case where the active substance is denser than the vehicle) or less creaming (in the case where the active substance is less dense than the vehicle), and accordingly improved performance due to the more uniform dispersion of the solid in the vehicle.

For the purpose of defining the present invention, the vehicles HFA 134a and HFA 227ea are referred to as suitable reference standards in which to measure flocculation volume. An active substance according to the invention may, however, be used in suspension in any suitable nonsolvent vehicle to give improved flocculation performance.

According to the first and/or second aspects of the invention, the flocculation volume after 5 minutes is preferably 40% or greater, more preferably 50% or greater, still more preferably at least 60% or 70% or 75% or 80% or 85% or 90% or 95% or 98%. The figure achieved may depend on the nature of the active substance, and factors such as its particle size and morphology, as described below.

This flocculation volume is preferably exhibited after 6 minutes, more preferably after 8 minutes, still more preferably after 10 minutes, most preferably after 15, 30 or 60 minutes or in some cases after 2, 6, 12 or even 24 hours. It is certainly exhibited after only 0.5 or 1 or 2 minutes. The flocculation volume is preferably measured at a concentration of above 0.5% w/v, more preferably from 0.5 to 3 or 4% w/v, most preferably from 0.5 to 1.5 or 2% w/v or from 0.8 to 1.3 or 1.5% w/v, such as 1% w/v. The above described flocculation performance may also be exhibited at lower active substance concentrations, for instance down to 0.15 or even 0.1% w/v.

The flocculation volume is preferably greater than 50% after 20 seconds, more preferably after 30 or 40 or 60 or 90 seconds, most preferably after 2 or 3 or even 5 minutes.

The active substances of the invention preferably exhibit the above described flocculation performance in other nonsolvent fluid vehicles, in particular hydrofluorocarbon propellants or mixtures thereof (for example, in a mixture of HFA 134a and HFA 227ea).

Preferably the active substances of the invention exhibit the above described flocculation behavior in the absence of dispersion enhancing or stabilizing additives (e.g., surfactants) in the active substance/vehicle mixture, or at least at lower levels of such additives than have previously been necessary for the same active substance/vehicle pair, for instance at additive (in particular surfactant) levels of less than 0.1% w/w based on the weight of the active substance, preferably less than 0.01% w/w or less than 0.001 or 0.0001% w/w.

They preferably exhibit this flocculation behavior in the absence of co-solvents, in particular polar co-solvents such as alcohols (e.g., ethanol).

Thus, their flocculation volumes are preferably measured in suspensions containing only, or consisting essentially of, the active substance and the relevant vehicle.

Further, the active substances of the invention preferably exhibit the above described behavior in the absence of (or at low levels of, such as less than 0.1 or 0.01 or 0.001% w/v based on the total suspension volume) lubricity enhancing additives, either in the active substance/vehicle mixture or on the internal surfaces of the container in which the flocculation performance of the mixture is tested. Typical such lubricants which are currently used in aerosol formulations include polyvinyl pyrrolidones and polyethylene glycols; coatings which are often used on the surfaces of for example aerosol canisters include epoxy resins or phenolic vinyl type coatings.

Thus, the flocculation volume of the active substance in the vehicle may be measured in a container made of for example glass or aluminum, the internal surfaces of which need not carry or incorporate any lubricity enhancing materials.

The mass median diameter (MMD) of the active substance particles is preferably less than 15 μm or in particular less than 10 μm, more preferably less than 5 or 4 μm, most preferably less than 3.5 or 3.3 or 3 or 2 or even 1 μm. It may be greater than 1 or 2 or even 2.5 μm. The mass median aerodynamic diameter (MMAD) of the active substance particles is preferably less than 10 microns, more preferably less than 5 microns, and most preferably less than 3.5 microns. For a given particle size, active substances according to the invention can demonstrate significantly better flocculation performance than the corresponding chemical entities made by conventional techniques such as spray drying, freeze drying and in particular micronization.

Particle sizes may be measured for instance using (a) an AEROSIZER™ time-of-flight instrument (which gives an aerodynamic equivalent particle diameter, MMAD) or (b) a laser diffraction sensor such as the HELOS™ system available from SYMPATEC™ GmbH, Germany (which provides a geometric projection equivalent MMD). MMADs may also be assessed using a cascade impactor. Volume mean diameters may be obtained in both cases using commercially available software packages. Active substances according to the present invention preferably have a volume-weighted median aerodynamic diameter (VMAD, measured for instance by laser diffraction analysis) of 5 μm or less, more preferably of 4 μm or 3.5 μm or less.

The active substances of the invention are preferably in the form of solid (e.g., as opposed to hollow, porous (which includes perforated) or at least partially fluid-containing) particles. They are preferably, although not necessarily, in a crystalline or semi-crystalline (as opposed to amorphous) form. More preferably they are crystalline, ideally highly crystalline, since the crystalline form of a material is often more stable in suspension than its amorphous or partially crystalline forms which may more readily dissolve in the fluid vehicle, with a risk of re-crystallization and/or particle growth.

An active substance according to the invention is thus preferably from 80% to 100% or from 90% to 100%, ideally 100% crystalline. It may therefore contain less than 20% w/w, preferably less than 10% w/w, more preferably less than 5 or 2 or 1 or even 0.5% w/w, most preferably no, detectable amorphous phase regions.

Crystallinity may be assessed in known ways for instance using X-ray diffraction (XRD) techniques, preferably high resolution X-ray powder diffraction such as using a synchrotron radiation source. Degree of crystallinity may be assessed for instance with respect to crystals of the same chemical entity produced by slow evaporative crystallization from solution. X-ray diffraction line broadening can provide an indication of reduced crystallinity, for example of crystal lattice imperfections. Line broadening may be manifested for instance by an increased peak width (e.g., full width at half maximum height, FWHM) for one or more of the diffraction peaks. A reduced level of crystal lattice imperfections, in a particulate product according to the invention, may also be manifested by a shift in position, towards higher 2θ values (typically a shift of 0.0005° or more, such as of from 0.0005° to 0.005° or from 0.001° to 0.003°), of one or more of the X-ray diffraction peaks, for instance compared to particles of the same chemical entity produced by micronization.

Levels of amorphous and crystalline phases, in an active substance according to the invention, may also be assessed by reference to its moisture uptake at any given temperature and humidity, and/or its thermal activity profile, again in known ways.

An active substance according to the invention preferably has an acicular crystalline form, i.e., a crystalline form which is significantly longer in one dimension than in at least one other dimension; this embraces for example needle-like crystals and also, potentially, wafer-, blade- or plate-like crystals (which are significantly longer in two dimensions than in the third) and elongate prism-shaped crystals. These have in cases been found to show better flocculation performance than similarly sized (e.g., with the same measured MMAD, or within 80% to 120% of the measured MMAD) particles of other shapes. Needle-like crystals may be preferred for their flocculation performance, and in this case the mass median particle diameter may be greater than 3 or 4 or 5 μm, perhaps greater than 6 or 7 or 8 or even 10 μm, although preferably (especially for delivery by inhalation) it will be 6 μm or less, more preferably 5 μm or less. Plate- or blade-like particles may be preferred for use in inhalers, and may have a mass median particle diameter of greater than 3 or 4 or 5 or 6 μm, although again for inhalation a preferred diameter may be 6 μm or less, more preferably 5 μm or less.

In the above discussion, "significantly" longer means at least 5%, preferably at least 10% or 20% or 30%, greater than the lower of the two dimensions being compared. Particles of an active substance according to the present invention preferably have an aspect ratio (the ratio of the longest to the shortest particle dimension) of 2:1 or greater, more preferably 3:1 or 4:1 or greater, most preferably from 1.5:1 to 5:1 or from 2:1 to 4.5:1.

The active substance is preferably in a substantially (e.g., 95% w/w or greater, preferably 98% or 99% w/w or 99.5% w/w or greater) pure form. It preferably contains low levels of residual solvent, for example less than 500 ppm, more preferably less than 200 ppm, most preferably less than 150 or 100 ppm residual solvent, by which is meant solvent(s) which were present at the point of particle formation. Still more preferably the substance contains no detectable residual solvent, or at least only levels below the relevant quantification limit(s). It is believed that lower residual solvent levels help to stabilize the particles in fluid suspensions, in particular in the presence of moisture, reducing the tendency for amorphous phase regions to re-crystallize and hence for particle growth and agglomeration.

If the active substance is a substance capable of existing in two or more different polymorphic forms, it preferably consists of only one such form, with a purity of 99.5% w/w or greater, preferably of 99.8% w/w or greater, with respect to the other polymorphic form(s). Polymorphic purity may be assessed for instance using melting point data (e.g., differential scanning calorimetry) or more preferably using X-ray powder diffraction (for instance the small-angle X-ray scattering (SAXS) technique) to detect polymorphic transitions during heating, based on the diffraction peaks characteristic of the polymorphs.

By "active substance" in the present context is meant a substance capable of performing some useful function in an end product, such as pharmaceutical or pesticidal substances.

The active substance may be a single active substance or a mixture of two or more. It may be monomeric, oligomeric or polymeric, organic (including organometallic) or inorganic, hydrophilic or hydrophobic, polar or non-polar. It may be a small molecule, for instance a synthetic drug like paracetamol, or a macromolecule such as a protein or peptide (including enzymes, hormones, antibodies and antigens), nucleotide, nucleoside or nucleic acid. Other potential active substances include vitamins, amino acids, lipids including phospholipids and aminolipids, carbohydrates such as mono-, di-, oligo- or polysaccharides, cells and viruses.

The active substance preferably comprises (more preferably is) a pharmaceutically or nutraceutically active substance, or a pharmaceutically or nutraceutically acceptable excipient, or a mixture of two or more thereof. More preferably the active substance is a pharmaceutically active substance which is suitable for delivery by inhalation (which term includes nasal and/or oral inhalation), whether for local administration (e.g., an asthma drug intended for local delivery to the lung) or for systemic delivery via the lung. However many other active substances, whatever their intended function (for instance, herbicides, pesticides, foodstuffs, imaging agents, dyes, perfumes, cosmetics and toiletries, detergents, coatings, products for use in the ceramics, photographic or explosives industries, etc.) are embraced by the present invention.

Of particular interest for delivery by inhalation (ideally using metered dose inhalers) are pharmaceutically active substances which need to be delivered systemically and require rapid onset of action. According to a preferred embodiment, formulations are provided which achieve a maximum concentration of a pharmaceutically active substance, $C_{max}$, within 1 hour of administration, preferably within 30 minutes, and most preferably within 15 minutes. This time to achieve maximum concentration of the active substance is referred to herein as $T_{max}$.

Examples of pharmaceutically active substances which may be delivered by inhalation include $\beta_2$-agonists, steroids such as glucocorticosteroids (preferably anti-inflammatories), anti-cholinergics, leukotriene antagonists, leukotriene synthesis inhibitors, pain relief drugs generally such as analgesics and anti-inflammatories (including both steroidal and non-steroidal anti-inflammatories), cardiovascular agents such as cardiac glycosides, respiratory drugs, anti-asthma agents, bronchodilators, anti-cancer agents, alkaloids (e.g., ergot alkaloids) or triptans such as sumatriptan or rizatriptan that can be used in the treatment of migraine, drugs (for instance sulphonyl ureas) useful in the treatment of diabetes and related disorders, sleep inducing drugs including sedatives and hypnotics, psychic energizers, appetite suppressants, anti-arthritics, anti-malarials, anti-epileptics, anti-thrombotics, anti-hypertensives, anti-arrhythmics, anti-oxicants, anti-depressants, anti-psychotics, anxiolytics, anti-convulsants, anti-emetics, anti-infectives, anti-histamines, anti-fungal and anti-viral agents, drugs for the treatment of neurological disorders such as Parkinson's disease (dopamine antagonists), drugs for the treatment of alcoholism and other forms of addiction, drugs such as vasodilators for use in the treatment of erectile dysfunction, muscle relaxants, muscle contractants, opioids, stimulants, tranquilizers, antibiotics such as macrolides, aminoglycosides, fluoroquinolones and beta-lactams, vaccines, cytokines, growth factors, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents and mixtures of the above (for example the asthma combination treatment containing both steroid and β-agonist).

More particularly, the active agent may fall into one of a number of structural classes, including but not limited to small molecules (preferably insoluble small molecules), peptides, polypeptides, proteins, polysaccharides, steroids, nucleotides, oligonucleotides, polynucleotides, fats, electrolytes, and the like.

Specific examples include the $\beta_2$-agonists salbutamol (e.g., salbutamol sulphate) and salmeterol (e.g., salmeterol xinafoate), the steroids budesonide and fluticasone (e.g., fluticasone propionate), the cardiac glycoside digoxin, the alkaloid anti-migraine drug dihydroergotamine mesylate and other alkaloid ergotamines, the alkaloid bromocriptine used in the treatment of Parkinson's disease, sumatriptan, rizatriptan, naratriptan, frovatriptan, almotriptan, zolmatriptan, morphine and the morphine analogue fentanyl (e.g., fentanyl citrate), glibenclamide (a sulphonyl urea), benzodiazepines such as valium, triazolam, alprazolam, midazolam and clonazepam (typically used as hypnotics, for example to treat insomnia or panic attacks), the anti-psychotic agent risperidone, apomorphine for use in the treatment of erectile dysfunction, the anti-infective amphotericin B, the antibiotics tobramycin, ciprofloxacin and moxifloxacin, nicotine, testosterone, the anti-cholenergic bronchodilator ipratropium bromide, the bronchodilator formoterol, monoclonal antibodies and the proteins LHRH, insulin, human growth hormone, calcitonin, interferon (e.g., (3- or γ-interferon), EPO and Factor VIII, as well as in each case pharmaceutically acceptable salts, esters, analogues and derivatives (for instance prodrug forms) thereof.

Additional examples of active agents suitable for practice with the present invention include but are not limited to aspariginase, amdoxovir (DAPD), antide, becaplermin, calcitonins, cyanovirin, denileukin diftitox, erythropoietin (EPO), EPO agonists (e.g., peptides from about 10-40 amino acids in length and comprising a particular core sequence as described in WO 96/40749), dornase alpha, erythropoiesis stimulating protein (NESP), coagulation factors such as Factor Vila, Factor VIII, Factor IX, von Willebrand factor; ceredase, cerezyme, alpha-glucosidase, collagen, cyclosporin, alpha defensins, beta defensins, exedin-4, granulocyte colony stimulating factor (GCSF), thrombopoietin (TPO), alpha-1 proteinase inhibitor, elcatonin, granulocyte macrophage colony stimulating factor (GMCSF), fibrinogen, filgrastim, growth hormones, growth hormone releasing hormone (GHRH), GRO-beta, GRO-beta antibody, bone morphogenic proteins such as bone morphogenic protein-2, bone morphogenic protein-6, OP-1; acidic fibroblast growth factor, basic fibroblast growth factor, CD-40 ligand, heparin, human serum albumin, low molecular weight heparin (LMWH), interferons such as interferon alpha, interferon beta, interferon gamma, interferon omega, interferon tau; interleukins and interleukin receptors such as interleukin-1 receptor, interleukin-2, interleukin-2 fusion proteins, interleukin-1 receptor antagonist, interleukin-3, interleukin-4, interleukin-4 receptor, interleukin-6, interleukin-8, interleukin-12, interleukin-13 receptor, interleukin-17 receptor; lactoferrin and lactoferrin fragments, luteinizing hormone releasing hormone (LHRH), insulin, pro-insulin, insulin analogues (e.g., monoacylated insulin as described in U.S. Pat. No. 5,922,675), amylin, C-peptide, somatostatin, somatostatin analogs including octreotide, vasopressin, follicle stimulating hormone (FSH), influenza vaccine, insulin-like growth factor (IGF), insulinotropin, macrophage colony stimulating factor (M-CSF), plasminogen activators such as alteplase, urokinase, reteplase, streptokinase, pamiteplase, lanoteplase, and teneteplase; nerve growth factor (NGF), osteoprotegerin, platelet-derived growth factor, tissue growth factors, transforming growth factor-1, vascular endothelial growth factor, leukemia inhibiting factor, keratinocyte growth factor (KGF), glial growth factor (GGF), T Cell receptors, CD molecules/antigens, tumor necrosis factor (TNF), monocyte chemoattractant protein-1, endothelial growth factors, parathyroid hormone (PTH), glucagon-like peptide, somatotropin, thymosin alpha 1, thymosin alpha 1 IIb/IIIa inhibitor, thymosin beta 10, thymosin beta 9, thymosin beta 4, alpha-1 antitrypsin, phosphodiesterase (PDE) compounds, VLA-4 (very late antigen-4), VLA-4 inhibitors, bisphosphonates, respiratory syncytial virus antibody, cystic fibrosis transmembrane regulator (CFTR) gene, deoxyribonuclease (Dnase), bactericidal/permeability increasing protein (BPI), and anti-CMV antibody.

Exemplary monoclonal antibodies include etanercept (a dimeric fusion protein consisting of the extracellular ligand-binding portion of the human 75 kD TNF receptor linked to the Fc portion of IgG1), abciximab, afeliomomab, basiliximab, daclizumab, infliximab, ibritumomab tiuexetan, mitumomab, muromonab-CD3, iodine 131 tositumomab conjugate, olizumab, rituximab, and trastuzumab (herceptin), amifostine, amiodarone, aminoglutethimide, amsacrine, anagrelide, anastrozole, asparaginase, anthracyclines, bexarotene, bicalutamide, bleomycin, buserelin, busulfan, cabergoline, capecitabine, carboplatin, carmustine, chlorambucin, cisplatin, cladribine, clodronate, cyclophosphamide, cyproterone, cytarabine, camptothecins, 13-cis retinoic acid, all trans retinoic acid; dacarbazine, dactinomycin, daunorubicin, dexamethasone, diclofenac, diethylstilbestrol, docetaxel, doxorubicin, epirubicin, estramustine, etoposide, exemestane, fexofenadine, fludarabine, fludrocortisone, fluorouracil, fluoxymesterone, flutamide, gemcitabine, epinephrine, L-Dopa, hydroxyurea, idarubicin, ifosfamide, imatinib, irinotecan, itraconazole, goserelin, letrozole, leucovorin, levamisole, lomustine, mechlorethamine, medroxyprogesterone, megestrol, melphalan, mercaptopurine, methotrexate, metoclopramide, mitomycin, mitotane, mitoxantrone, naloxone, nicotine, nilutamide, octreotide, oxaliplatin, pamidronate, pentostatin, pilcamycin, porfimer, prednisone, procarbazine, prochlorperazine, ondansetron, raltitrexed, sirolimus, streptozocin, tacrolimus, tamoxifen, temozolomide, teniposide, testosterone, tetrahydrocannabinol, thalidomide, thioguanine, thiotepa, topotecan, tretinoin, valrubicin, vinblastine, vincristine, vindesine, vinorelbine, dolasetron, granisetron; formoterol, fluticasone, leuprolide, midazolam, alprazolam, amphotericin B, podophylotoxins, nucleoside antivirals, aroyl hydrazones, sumatriptan; macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin; aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate; polymixins such as polymixin B, capreomycin, bacitracin, penems; penicillins including penicllinase-sensitive agents like penicillin G, penicillin V; penicllinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, aziocillin, meziocillin, and piperacillin; cephalosporins like cefpodoxime, cefprozil, ceftbuten, ceftizoxime, ceftriaxone, cephalothin, cephapirin, cephalexin, cephradine, cefoxitin, cefamandole, cefazolin, cephaloridine, cefaclor, cefadroxil, cephaloglycin, cefuroxime, ceforamide, cefotaxime, cefatrizine, cephacetrile, cefepime, cefixime, cefonicid, cefoperazone, cefotetan, cefinetazole, ceftazidime, loracarbef, and moxalactam, monobactams like aztreonam; and carbapenems such as imipenem, meropenem, pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, and ergotamine tartrate; taxanes such as paclitaxel; SN-38, and tyrphostines.

The above exemplary biologically active agents are meant to encompass, where applicable, analogues, agonists, antagonists, inhibitors, isomers, and pharmaceutically acceptable salt forms thereof. In reference to peptides and proteins, the invention is intended to encompass synthetic, recombinant, native, glycosylated, non-glycosylated, and biologically active fragments and analogs thereof.

Drugs for which an immediate release into the bloodstream (i.e., rapid onset of pharmaceutical effect) might be particularly desirable include those for use in the treatment of migraine, nausea, insomnia, allergic (including anaphylactic) reactions, neurological or psychiatric disorders (in particular panic attacks and other psychoses or neuroses), erectile dysfunction, diabetes and related disorders and cardiac disorders, anti-convulsants, bronchodilators and drugs for the alleviation of pain or inflammation.

The active substance may comprise two or more substances formulated together, such as one coated with another, or one dispersed within a matrix of another, or a blend of two or more active substances. Common examples of such formulations include pharmaceutically active substances coated with excipients, or solid dispersions of pharmaceutically active substances with excipients, the excipient often being present to modify the release rate and/or to target delivery of the pharmaceutical. However, in general the active substances of the invention will exhibit the improved flocculation behavior in the absence of excipients, i.e., in the form of the active substance alone (for example, in the form of pharmaceutically or nutraceutically active substance(s) without excipients).

A third aspect of the present invention provides an active substance in particulate form, which is insoluble in the fluid vehicle 1,1,1,2-tetrafluoroethane (HFA 134a) and which when suspended in that vehicle at a concentration of from 0.2% to 5% w/v exhibits a flocculation volume after 5 minutes which is at least 20% higher, preferably at least 50% or 150% or 200% or 250% higher, than that exhibited by the same chemical entity having the same or a similar particle size (typically measured MMAD, "similar" here meaning within 80% to 120%, preferably within 90% to 110%, of the measured MMAD) but prepared using a micronization process.

A fourth aspect provides an active substance in particulate form, which is insoluble in the fluid vehicle 1,1,1,2,3,3,3-heptafluoropropane (HFA 227ea) and which when suspended in that vehicle at a concentration of from 0.2% to 5% w/v exhibits a flocculation volume after 5 minutes which is at least 20% higher, preferably at least 50% or 150% or 200% or 250% higher, than that exhibited by the same chemical entity having the same or a similar particle size (as described above) but prepared using a micronization process.

By "micronization" in this context is meant a process involving mechanical means, for instance milling or grinding, to reduce particle size to the micrometer range.

According to the third and/or fourth aspects of the invention, the active substance preferably exhibits this flocculation behavior after 6 minutes, more preferably after 8 minutes, still more preferably after 10 minutes, most preferably after 15, 30 or 60 minutes or in some cases after 2, 6, 12 or even 24 hours. It may exhibit this behavior after only 4, 3, 2 or in some cases 1 minute. The flocculation volume is preferably measured at a concentration of above 0.5% w/v, more preferably from 0.5 to 3 or 4% w/v, most preferably from 0.5 to 1.5 or 2% w/v or from 0.8 to 1.3 or 1.5% w/v, such as 1% w/v. The above described flocculation performance may also be exhibited at lower active substance concentrations, for instance down to 0.15 or even 0.1% w/v.

Again, the active substance preferably exhibits this flocculation performance in other nonsolvent fluid vehicles, in particular hydrofluorocarbon propellants.

A fifth aspect of the present invention provides an active substance in particulate form, which is insoluble in the fluid vehicle 1,1,1,2-tetrafluoroethane (HFA 134a) and which when suspended in that vehicle at a concentration of from 0.2 to 5% w/v exhibits a rate of change (decrease) in flocculation volume, during the first 60 seconds after thorough mixing of the active substance and vehicle, of 20% per minute or less.

A sixth aspect provides an active substance in particulate form, which is insoluble in the fluid vehicle 1,1,1,2,3,3,3-heptafluoropropane (HFA 227ea) and which when suspended in that vehicle at a concentration of from 0.2 to 5% w/v exhibits a rate of change (decrease) in flocculation volume, during the first 60 seconds after thorough mixing of the active substance and vehicle, of 20% per minute or less.

According to the fifth and/or sixth aspects of the invention, the rate of change in flocculation volume is preferably 15% per minute or less, more preferably 10% per minute or less, most preferably 5 or 3% per minute or less. Preferably it is within the quoted ranges for the first 90 or 120 seconds after thorough mixing of the active substance and vehicle; certainly it is within those ranges during the first 30 seconds.

Other preferred features of the active substances of the third to the sixth aspects of the invention, including the manner in which (and concentration at which) their flocculation volumes may be measured, may be as described for those of the first and second aspects.

When formulated in fluid suspensions, the active substances of the present invention can benefit from generally improved stability, in particular relative to their micronized equivalents, during medium to long term storage (for instance, for periods of a week or more, preferably a month or more, most preferably 3 or 6 or 12 or 18 or 24 or 30 or even 36 months or more). They appear to remain more homogeneously dispersed for longer periods of time. They also typically show a reduced tendency for particle growth and agglomeration in fluid suspensions, for example, their MMADs may vary by no more than 30%, preferably no more than 20% or 10%, of the starting value during storage as a fluid suspension for a period of a week or more, preferably a month or more, most preferably 3 or 6 or 12 or 18 or 24 or 30 or even 36 months or more. Again the fluid in which, and concentration at which, they are suspended may be as described above in connection with the first to the sixth aspects of the invention; the fluid is preferably either HFA 134a, HFA 227ea, or a mixture thereof.

Thus, when used in aerosol formulations for use in inhalers (in particular MDIs), the active substances of the invention can give a more uniform dosing rate throughout the useable life of the inhaler. They can also provide, in this context, greater uniformity in the efficacy of the delivered drug throughout the inhaler life, particle size being relevant to bioavailability and to efficiency of delivery through the lung (in particular the deep lung).

A typical aerosol canister, for example as used in a metered dose inhaler, can often allow the ingress of atmospheric moisture through its delivery mechanism during medium to long term storage. This moisture can reduce the stability of the suspension inside the canister. The active substances of the present invention can be significantly more stable than for instance their micronized equivalents under such storage conditions, being less susceptible to particle growth and agglomeration even in the presence of moisture. It has been found that even amorphous phase active substances according to the invention can be relatively stable under such conditions, despite the fact that moisture would normally be expected to induce re-crystallization.

The stability of the active substances of the invention is therefore of particular use in aerosol formulations in delivery devices such as inhalers, in particular metered dose inhalers. Thus, when an active substance according to the invention is suspended in a fluid vehicle, suitably an aerosol propellant such as HFA 134a or HFA 227ea or a mixture thereof, and delivered in a succession of doses of equal volume using a metered dose inhaler or into a measuring device such as a cascade impactor (e.g., an ANDERSEN™ cascade impactor or a similar type of cascade impactor).

a) the relative standard deviation RSD (i.e., the standard deviation expressed as a percentage of the mean value) in the quantity of active substance delivered in each dose is preferably no more than 15% over 3, more preferably over 5, most preferably over 10 or 30 or 50 or 70 or 100 or 150 or 200 successive doses. Yet more preferably, the RSD is no more than 12 or 10 or 8 or 7 or 6 or 5 or 4 or even 3%.

b) the RSD in the fine particle content (the quantity of delivered active substance having a MMAD in the fine particle range, such as <3.5 or 3.3 µm) of the delivered doses is preferably no more than 15% over 3, more preferably over 5, most preferably over 10 or 30 or 50 or 70 or 100 or 150 or 200 successive doses. Yet more preferably, the RSD is no more than 9 or 8 or 7 or 6 or 5 or even 2%.

c) the RSD in the fine particle fraction contained in each dose (i.e., the quantity of active substance having a MMAD in the fine particle range, expressed as a percentage of the total active substance content in the relevant dose) is preferably no more than 17% over 3, more preferably over 5, most preferably over 10 or 30 or 50 or 70 or 100 or 150 or 200 successive doses. Yet more preferably, the RSD is no more than 15 or 13 or 10 or 8 or 6 or 5%.

d) the RSD in the MMAD of the active substance particles contained in each dose is preferably no more than 9.5% over 3, more preferably over 5, most preferably over 10 or 30 or 50 or 70 or 100 or 150 or 200 successive doses. Yet more preferably, the RSD is no more than 7 or 4 or 3 or 2%.

e) the fine particle fraction contained in each dose is preferably at least 25%, more preferably at least 26 or 27%, most preferably at least 30 or even 35% over 3, more preferably over 5, most preferably over 10 or 30 or 50 or 70 or 100 or 150 or 200 successive doses.

f) the MMAD of the particles delivered in each dose is preferably 4 µm or less, more preferably 3.8 or 3.5 µm or less, again suitably over 3, more preferably over 5, most preferably over 10 or 30 or 50 or 70 or 100 or 150 or 200 successive doses.

For the purpose of measuring the properties (a) to (f) above, the delivery or measuring device is ideally operated in the standard way, according to the manufacturer's instructions, which will typically for instance involve agitating the aerosol formulation before delivering each dose. Suitable measurement methods are those described in Examples 9 to 13 below, and typically involve the use of a cascade impactor such as an ANDERSEN™ cascade impactor or a similar type of cascade impactor. For example, an aerosol can containing the formulation under test may be coupled to a cascade impactor via a standard adaptor and USP induction port ("throat"), and the contents of the can dispensed into the impactor via a conventional aerosol valve (typically crimped into the top of the can) and actuator.

The relevant number of doses, over which the parameter in question is measured, may be delivered over a period of up to 1, 3, 6, 12, 18, 24 or even 30 or 36 months, although under laboratory test conditions may be delivered over a period of for instance from 30 minutes to 12 hours, more typically from 30 minutes to 4 or 5 hours, most typically from 2 to 3 hours (e.g., with an interval of from 15 to 120 seconds, preferably from 30 to 60 seconds, between doses). A suitable dose volume might be from 20 to 100 µL, more typically from 45 to 70 µL such as from 50 to 65 µL. Preferred features of the formulated suspensions, such as the vehicle type, the active substance concentration and the nature and quantity of additives (preferably none), may all be as described in connection with the first to the sixth aspects of the invention.

For assessing performance over a larger number of doses (for example, 50 or 100 or more), it may be sufficient to measure the relevant parameter(s) over a few (for instance from 2 to 6, preferably from 3 to 5) successive doses at periods towards the start and end, and ideally also in the middle, of the total delivery period.

The RSD values referred to in (a) to (d) above are typically lower than (preferably at least 5% or 10% or 20% lower than) those obtained when a micronized form of the same chemical entity, having the same or a similar MMAD, is subjected to the same test(s). In each case, uniformity of dosing characteristics is expected to be improved over any given period of use by using an active substance in accordance with the invention.

The active substances of the invention preferably exhibit the flocculation performance and/or stability described above when stored during the relevant measurement period, in suspension in a fluid vehicle (whether or not within a delivery device such as an inhaler), at ambient temperature (e.g., from 18 to 25° C., or from 20 to 23° C., such as about 22° C., or at the accepted industrial standard temperature of 25° C.). More preferably, they exhibit that behavior and/or stability even if subjected during the measurement period to fluctuations of up to ±5° C. or ±10° C. or ±15° C.

They may exhibit the above described flocculation performance and/or stability when their fluid suspensions are stored before or during the relevant measurement period at up to 20% or 30% or 40% or 60% or even 75% relative humidity (RH). Higher storage temperatures and/or humidities may be used, in conventional manner, to mimic longer term storage periods, as may conventional thermal cycling procedures such as freeze/thaw cycling. For example, storage for a given period at 40° C. and 75% RH is generally used to mimic storage for approximately 3 times as long at 25° C. and 60% RH. Thermal cycling may for example involve cycling the storage temperature up to 2 or even 4 times daily, for instance between 2° C. and 40° C. or (in the case of freeze/thaw cycling) between −20° C. and 25° C. Measurements (for example, of MMAD or fine particle fraction or dose content) may be taken both before and after a period of storage under given conditions, or both before and after thermal cycling, and the recorded values and RSDs between the two measurements or sets of measurements are preferably as described under points (a) to (f) above.

In certain cases, an active substance according to the present invention may be a pharmaceutically active substance or a pharmaceutically acceptable excipient (preferably a substance suitable for and/or intended for delivery by inhalation) other than salmeterol xinafoate (alone or co-formulated with hydroxypropyl cellulose); a-lactose monohydrate; R-TEM P-lactamase; maltose; trehalose; sucrose; budesonide; salbutamol sulphate; nicotinic acid; paracetamol (alone or co-formulated with salmeterol xinafoate, L-poly(lactic acid), ethyl cellulose (EC), hydroxypropyl methyl cellulose (HPMC) or poly vinyl pyrrolidone (PVP)); ibuprofen; ketoprofen (alone or co-formulated with EC, HPMC or PVP); salicylic acid; either indomethacin, carbamazepine, theophylline, ascorbic acid or a COX-2 selective inhibitor co-formulated with EC, HPMC or PVP; quinine sulphate co-formulated with EC; fluticasone propionate; omeprazole magnesium tetrahydrate; (S)-omeprazole magnesium trihydrate; formoterol fumarate dihydrate; felodipine; candesartan cilexetil; lysozyme (alone or co-formulated with sodium taurocholate); albumin; insulin (alone or co-formulated with sodium taurochlorate); terbutaline sulphate; fenoterol hydrobromide and/or ipratropium bromide.

It has been found that particulate active substances which exhibit the improved flocculation behavior described in connection with the first to the sixth aspects of this invention can be produced using the so-called SEDS® ("Solution Enhanced Dispersion by Supercritical Fluid") process (now known as the NEKTAR® SCF process), which is a version of the GAS process referred to above.

Certain inhalation drugs have been produced before using SEDS®—see for example WO-95/01221 (salmeterol xinafoate), WO-98/36825 (salbutamol sulphate), WO-98/52544 (budesonide) and WO-98/17676 (fluticasone propionate). In the latter, some of the products are tested in a metered dose inhaler in the propellant HFA 134a, but flocculation volumes are not measured or indeed mentioned and only relatively low drug/propellant concentrations are used.

The NEKTAR® SCF process (SEDS®) is a process for forming particles of a "target" substance. It is a GAS process and so involves contacting a solution or suspension of the target substance in a fluid vehicle (the "target solution/suspension") with a compressed fluid (generally a supercritical or near-critical fluid) anti-solvent under conditions which allow the anti-solvent to extract the vehicle from the target solution/suspension and to cause particles of the target substance to precipitate from it. The conditions are such that the fluid mixture formed between the anti-solvent and the extracted vehicle is still in a compressed (generally supercritical or near-critical) state. The anti-solvent fluid should be a nonsolvent for the target substance and be miscible with the fluid vehicle.

Carrying out a SEDS® process specifically involves using the anti-solvent fluid simultaneously both to extract the vehicle from, and to disperse, the target solution/suspension. In other words, the fluids are contacted with one another in such a manner that the mechanical (kinetic) energy of the anti-solvent can act to disperse the target solution/suspension at the same time as it extracts the vehicle. "Disperse" in this context refers generally to the transfer of kinetic energy from one fluid to another, usually implying the formation of droplets, or of other analogous fluid elements, of the fluid to which the kinetic energy is transferred.

Suitable SEDS® processes are described in WO-95/01221, WO-96/00610, WO-98/36825, WO-99/44733, WO-99/59710, WO-01/03821, WO-01/15664, WO-02/38127 and WO-03/008082. Other suitable SEDS® processes are described in WO-99/52507, WO-99/52550, WO-00/30612, WO-00/30613, WO-00/67892 and WO-02/058674, all of which are hereby incorporated in their entirety by reference.

In SEDS®, the target solution/suspension and the anti-solvent are preferably contacted with one another in the manner described in WO-95/01221 and/or WO-96/00610, being co-introduced into a particle formation vessel using a fluid inlet means which allows the mechanical energy (typically the shearing action) of the anti-solvent flow to facilitate intimate mixing and dispersion of the fluids at the point where they meet. The target solution/suspension and the anti-solvent preferably meet and enter the particle formation vessel at substantially the same point, for instance via separate passages of a multi-passage coaxial nozzle.

Alternatively, the SEDS® process may be of the type described in WO-03/008082, in which the anti-solvent velocity as it enters the particle formation vessel is near-sonic, sonic or supersonic and the target solution/suspension and the anti-solvent enter the vessel at separate, although close, locations. Such a process is described for instance in Example 1a below, in connection with the preparation of sample B.

A particulate active substance according to the present invention is preferably prepared using a GAS process, and more preferably using a SEDS® process, such as one or a combination of those described in the above documents. Preferred features of the process may be as described below in connection with the seventh aspect of the invention. The active substance may thus be insoluble or only sparingly soluble in water. It is preferably insoluble or only sparingly soluble in compressed (e.g., supercritical or near-critical) carbon dioxide. Such materials lend themselves particularly well to SEDS® processing and indeed are often difficult to process using other particle formation techniques such as spray drying or freeze drying.

Although it is known that SEDS® can yield particulate products with controlled physicochemical characteristics such as particle size, size distribution and morphology, it has not previously been recognized that products of the SEDS® process could exhibit such an improvement in flocculation performance compared to the corresponding substances produced by other particle formation techniques.

It is advantageous to be able to use the SEDS® process to achieve this additional improvement in product characteristics for materials which need to be delivered in suspension in a fluid vehicle. SEDS® is known to give the improved product properties described above, and in addition is a relatively efficient, safe, easily scalable, controlled and reproducible process. It can be used to prepare a wide range of substances including water insoluble materials which cannot for instance easily be prepared by spray drying, materials which are insoluble in supercritical $CO_2$ which cannot easily be prepared by RESS, and temperature- or otherwise-sensitive materials for which other conventional particle formation processes might be inappropriate. SEDS® can also yield products which are highly crystalline in nature, and/or high in purity (including polymorphic purity) with low residual solvent content.

Thus, a seventh aspect of the present invention provides the use of a SEDS® process, as described above, to produce an active substance in particulate form, for the purpose of improving the flocculation performance of the substance.

The process is preferably carried out using supercritical, near-critical or liquid, more preferably supercritical, $CO_2$ as the anti-solvent. The choice of operating conditions such as temperature, pressure and fluid flow rates, and the choice of solvent and of anti-solvent modifier if necessary, will depend on the nature of the active substance, for instance its solubility in the fluids present and, if it can exist in different polymorphic forms, which form is to be precipitated. Generally, the conditions should be chosen to minimize particle sizes—this will usually mean selecting a higher relative anti-solvent flow rate (e.g., a target solution/suspension:anti-solvent flow rate ratio (at or immediately prior to the two fluids coming into contact with one another) of 0.03 or less, preferably 0.02 or less or even 0.01 or less), and/or a higher operating temperature (e.g., from 50° C. to 100° C., preferably from 70° C. to 90° C.), and/or a higher operating pressure (e.g., from 80 to 210 bar, preferably from 90 to 200 bar).

The SEDS® processing conditions are also preferably selected to reduce residual solvent levels and/or generally to increase the product purity (including if applicable its polymorphic purity). They may be selected to increase the crystallinity of the product, in which case a lower relative anti-solvent flow rate may be preferred (for example, a target solution/suspension:anti-solvent flow rate ratio of 0.01 or greater, preferably 0.015 or 0.02 or greater) so as to slow down the solvent extraction process.

The product of the seventh aspect of the invention is preferably a product according to one of the first to the sixth aspects.

"Improving the flocculation performance" in this context means increasing the flocculation volume exhibited by the substance in the relevant vehicle at a given concentration after a given period of time. It may include improving the performance (in particular, the uniformity in performance and/or storage stability) of fluid suspensions of the active substance in delivery devices such as metered dose inhalers. The SEDS® process is preferably used so as to achieve flocculation behavior, and/or stability, and/or performance in a delivery device, of the types described above in connection with the first, second, third, fourth, fifth and/or sixth aspects of the invention.

Such changes in performance and attributes may be as compared to those of the substance prior to the SEDS® processing, and/or of the same substance (preferably having the same particle size or a particle size no more than 10% or 20% different) when produced using another particle formation process such as micronizing or spray drying.

Flocculation volume, sometimes referred to as "sedimentation volume", can be measured by a conventional and relatively simple method. The substance under test, in particulate form, is suspended in the desired fluid vehicle at a suitable concentration. The mixture should be well agitated (typically, simply by shaking) to ensure a uniform dispersion of particles in the fluid at the start of measurement. Immediately after agitation ceases, timing begins. The mixture is left to stand, usually under ambient conditions, and the degree of settling or creaming of the solid observed over time.

The flocculation volume of the mixture at a given point in time is the volume of fluid which is still occupied by the particulate dispersion, expressed as a percentage of the total fluid volume. A higher flocculation volume thus indicates less settling/creaming, which indicates improved performance.

All references herein to flocculation volumes, unless otherwise stated, are to measurements made at 22° C.

To achieve meaningful measurements of flocculation volume, the active substance should be insoluble in the chosen fluid vehicle, at least to an extent sufficient to allow suspension of the active substance as solid particles in the fluid. The solubility of the substance in the vehicle is preferably less than 10-5% w/v.

In certain active substance/vehicle systems, surfactants and/or other dispersion enhancing or stabilizing additives may be used in order to achieve sufficient dispersion at the start of the test—these include many systems in which the vehicle is water or another aqueous fluid. However, SEDS® products have been found to exhibit the desired flocculation behavior even in the absence of such additives, particularly in non-aqueous vehicles.

According to an eighth aspect of the present invention, there is provided an active substance for use in a method of surgery, therapy or diagnosis practiced on a human or animal body, in which method the substance is delivered to a patient in suspension in a nonsolvent fluid vehicle in which the flocculation performance of the substance is as defined above in relation to any one of the first to the sixth aspects of the invention.

A ninth aspect of the invention provides the use of an active substance in the manufacture of a medicament which comprises a suspension of that substance in a nonsolvent fluid vehicle, in which suspension the flocculation performance of the active substance is as defined above in relation to any one of the first to the sixth aspects of the invention. The medicament may be for use in a method of surgery, therapy or diagnosis practiced on a human or animal body, and is preferably suitable for delivery by inhalation.

A tenth aspect provides the use of an active substance according to any one of the first to the sixth aspects, in suspension in a nonsolvent fluid vehicle at a concentration of at least 0.2% w/v, preferably at least 0.5% w/v, and more preferably the suspension containing no, or less than 0.1% w/w based on the weight of the active substance, preferably less than 0.01% w/w or less than 0.001 or 0.0001% w/w, dispersion enhancing or stabilizing additives such as surfactants. Again the suspension preferably contains no co-solvents or lubricity enhancing additives.

For the eighth and ninth aspects of the invention, the active substance is preferably an active substance according to one of the first to the sixth aspects. It is preferably a pharmaceutically active substance, more preferably one which is suitable for delivery by inhalation. The medical method in which it may ultimately be used may involve the treatment of any of the conditions mentioned in connection with the active substances of the invention.

Other preferred features of the eighth to the tenth aspects of the invention may be as described in connection with the first to the sixth aspects. In particular, the suspension is preferably an aerosol formulation in an aerosol propellant fluid, in particular in a hydrofluorocarbon propellant such as HFA 134a and/or HFA 227ea, and is preferably suitable for delivery to a patient by inhalation.

An eleventh aspect of the invention provides a formulation, typically an aerosol formulation, containing an active substance according to any one of the first to the sixth aspects suspended in a nonsolvent fluid vehicle.

The active substance is preferably a pharmaceutically active substance, although it may alternatively be a nutraceutical, a cosmetic or toiletry or any other active substance suitable for delivery in a nonsolvent propellant fluid.

The fluid vehicle is preferably an aerosol propellant fluid such as those described above. It is preferably free of chlorofluorocarbon propellants, and more preferably comprises a hydrofluorocarbon propellant such as HFA 134a, HFA 227a, 1,1,2,2,3-pentafluoropropane or a mixture of any thereof. Other suitable vehicles include other C1 to C4 hydrofluorocarbons such as CHF2CHF2, CF3CH2F, CHF2CH3 and CF3CHFCF3, and perfluorocarbons such as CF3CF3 and CF3CF2CF3. The vehicle is preferably of a pharmaceutically acceptable grade.

Most preferably the vehicle is HFA 134a, HFA 227a or a mixture thereof, such propellants are available, for instance, from DuPont Fluoroproducts, Wilmington, Del. It may be water or another aqueous fluid, although the active substance should be insoluble in the chosen vehicle at least to an extent sufficient to allow its suspension as solid particles.

According to the present invention, a fluid vehicle may comprise a mixture of two or more fluids. The mixture may be tailored for instance to minimize the difference in densities between the vehicle and the active substance and thus enhance the overall flocculation performance of the active substance. As an example, a mixture of the propellants HFA 134a and HFA 227a may be used to minimize the risk of either settling or "creaming" of a suspended active substance.

The concentration of the active substance in the formulation may be 0.1% w/v or greater, 0.2% w/v or greater, or even 0.5% w/v or 0.6% w/v or 0.7% w/v or 0.8% w/v or 1% w/v or greater, depending on the dosing level of the active substance. It is preferably from 0.1 or 0.2 to 5% w/v, more preferably from 0.5 or 0.7 to 1.6% w/v, most preferably from 0.5 or 0.7 to 1.5 or 1.3 or 1.1 or 0.9% w/v, although it may be up to 3% w/v. In cases, therefore, the present invention can allow relatively high concentration formulations to be prepared, of particular use for active substances which need to be delivered in high doses.

In cases however the concentration of the active substance in the formulation may be as low as 0.05 or 0.02% w/v.

The active substance generally need not be surface modified (e.g., by treatment with a nonsolvent such as a non-polar liquid) prior to incorporation in the formulation.

One or more surfactants, or other dispersion enhancing or stabilizing additives, may be included in the formulation, typical examples being nonionic surfactants such as those available in the Tween™ series. A lubricant may be included to prevent the active substance depositing on the internal surfaces of the aerosol can or other delivery device in which the formulation is to be used. Preferably, however, the formulation consists essentially of only the active substance and the vehicle, with only low levels (for instance, less than 0.1% w/w based on the weight of the active substance, preferably less than 0.01% w/w or less than 0.001 or 0.0001% w/w) of, or more preferably in the absence of, such additives. The formulation conveniently contains no, or only low levels (for instance, less than 0.01% w/w based on the weight of the fluid vehicle, preferably less than 0.001% w/w) of co-solvents, typical co-solvents being alcohols such as ethanol.

The stability of the formulation is preferably as described above in connection with the first to the sixth aspects of the invention, as is its aerosol performance (in particular dosage uniformity) in use in a delivery device such as a metered dose inhaler or when assessed for instance using a cascade impactor. In particular, the formulation preferably comprises a fine particle fraction (as defined above) of at least 25%, more preferably at least 30%, most preferably 35%.

It has moreover been found that formulations according to the present invention can be particularly efficient for delivering active substances to the central and in particular to the deep lung, and thus in turn for the systemic delivery of active substances via the lung. Typically particles with MMAD from 4 µm to 6 µm, more specifically from 4.7 µm to 5.8 µm, will reach the "central" lung area (trachea and primary bronchi) whereas only those with MMAD of 3.5 µm, preferably 3.3 µm or less will penetrate the "deep" lung region (alveoli, and secondary and terminal bronchi). The stability of the invented formulations, with respect to flocculation and aggregation of the suspended active substance particles, can allow them to deliver active substances having a high bioavailability and an efficient release profile.

Thus, when a formulation according to the invention is delivered to a live human or animal patient using a metered dose inhaler or an equivalent delivery device, the active substance may be released more rapidly into the patient's bloodstream, compared for instance to a micronized form of the same active substance (suitably having the same or a similar MMAD) delivered under the same test conditions. The bioavailability of the active substance (expressed for example as the maximum, or as the total plasma concentration attained following dose delivery) may be higher than, preferably at least 1.5 or 1.8 or 2 or 2.5 times as high as, that of the micronized equivalent. It has been found that active substances according to the invention may perform well in such tests whether with or without excipients such as the polymeric excipients (e.g., polyvinyl pyrrolidone or polyethylene glycols) traditionally used to improve the bioavailability and/or release rate of for instance poorly water soluble drugs.

According to a preferred embodiment, a formulation according to the invention may achieve a maximum concentration Cmax of the active substance in the patient's bloodstream within one hour of administration (typically of inhalation), preferably within 30 minutes, more preferably within 15 minutes of administration. This time to achieve maximum concentration is referred to hereafter as Tmax.

Preferred features of the eleventh aspect of the invention, in particular regarding the nature, particle size and/or morphology of the active substance, and/or its stability and performance in a delivery device, may be as described in connection with the first to the tenth aspects.

The eleventh aspect of the invention may also encompass formulations in which the fluid (typically liquid) vehicle is other than an aerosol propellant, for instance a liquid carrier for a pharmaceutically active substance intended for delivery by injection, orally or by any other suitable administration route. The vehicle may be organic or aqueous, it may comprise a mixture of two or more fluids, and it may include materials other than the active substance.

A twelfth aspect of the present invention provides a drug delivery device, preferably an inhaler, which contains one or more dosage formulations of an active substance according to any one of the first to the sixth aspects, and preferably also a suitable fluid vehicle in which to aerosolize the substance. Alternatively, the delivery device may contain, or be able to produce, one or more aerosol formulations according to the eleventh aspect of the invention. The delivery device is preferably of the type designed to deliver a predetermined dose of an active substance in a pressurized fluid vehicle, for instance a metered dose inhaler (which term includes pressurized metered dose inhalers (pMDIs)).

A thirteenth aspect of the invention provides an aerosol can containing an aerosol formulation according to the eleventh aspect of the invention, and which is suitable for use in a delivery device such as a MDI, preferably a device according to the twelfth aspect of the invention.

Because of the enhanced flocculation performance of the active substances of the invention, it may be unnecessary for the internal surfaces of the aerosol can (i.e., those surfaces which come into contact with the aerosol formulation during use) to be specially treated, for example with lubricity-enhancing coatings, to reduce retention of active substance deposits inside the can or its associated delivery mechanisms.

The capacity of the aerosol can might typically be from 10 mL to 20 mL. It may suitably be made from toughened glass or aluminum. It may comprise a conventional delivery mechanism, such as a metering valve of typical volume 25 µL to 100 µL, more typically from 45 µL to 70 µL, such as from 50 µL to 65 µL, together with a suitable valve actuator.

According to a fourteenth aspect, the invention provides a method for delivering an active substance, the method involving charging an aerosol can with an active substance and/or a formulation according to the invention. Subsequent delivery of the can contents may be via a delivery device such as a MDI.

A fifteenth aspect provides a method of treatment of a human or animal patient, which method involves administering to the patient, preferably using a method according to the fourteenth aspect of the invention, an active substance and/or a formulation according to the invention.

Both of these methods preferably involve the use of a drug delivery device such as an inhaler, more preferably a delivery device according to the twelfth aspect of the invention. The active substance preferably comprises a pharmaceutically active substance suitable for inhalation therapy.

The present invention will now be described by way of example only and with reference to the accompanying illustrative drawings.

EXAMPLES

In the following experiments, SEDS® processes were used to produce a number of drugs in particulate form and their behavior in typical MDI propellants was then examined.

In most cases the system used to carry out the particle formation was of the general type shown schematically in FIG. 1 of WO-95/01221. A two-passage coaxial nozzle (see FIG. 3 of WO-95/01221) was used to co-introduce into a 500 mL (except for Examples 1a) particle formation vessel (i) a solution of the drug in a solvent carrier and (ii) supercritical $CO_2$ as the anti-solvent. The anti-solvent extracted the carrier at the nozzle outlet causing particles to be precipitated. The temperature and pressure were controlled within the vessel to ensure the $CO_2$ remained in supercritical form throughout the process, even when mixed with the carrier.

The particulate products were all fine, free flowing powders with smooth particle surfaces.

Flocculation volumes were measured in the general manner described above. 0.4 g of the relevant sample was filled into a 100 mL glass aerosol bottle. The bottle was pressurized with 40 mL of the propellant fluid to give a 1% w/v dispersion and then shaken vigorously for 30 seconds to ensure complete dispersion of the powder. After agitation, the bottle was placed on a flat surface and the flocculation volume measured by eye every 15 seconds for the following 10 minutes. Measurements were taken at 22° C.

Example 1a

Preparation of Salmeterol Xinafoate

Salmeterol xinafoate (sample A) in its polymorphic form I was precipitated from methanol (2% w/v) using an operating temperature of 60° C., an operating pressure of 100 bar, a nozzle with a 200 μm outlet diameter, a particle formation vessel with 50 mL capacity, a salmeterol solution flow rate of 0.4 mL/min and a $CO_2$ flow rate of 20 mL/min (note: all $CO_2$ flow rates were measured at the pump head). The product had a MMAD of 5.3 μm (AEROSIZER™).

A further sample (B) of salmeterol xinafoate form I was made by a modified SEDS® process, as described in WO-03/008082, in which the salmeterol solution and $CO_2$ were introduced through an inlet tube and a perpendicularly orientated nozzle (outlet diameter 200 μm) respectively, with a $CO_2$ flow rate sufficient for it to acquire a sonic velocity at the nozzle outlet. For this particle formation process the salmeterol/methanol solution concentration was 3% w/v, the operating temperature 36° C., the operating pressure 80 bar, the salmeterol solution flow rate 4 mL/min and the $CO_2$ flow rate 158 mL/min. The $CO_2$ was pre-heated to 90° C. prior to entering the nozzle, to compensate for Joule-Thomson cooling on expansion of the fluid across the nozzle. The product had a MMAD of 1.6 μm (AEROSIZER™).

Example 1b

Flocculation Performance of Salmeterol Xinafoate

The flocculation performance of the products of Example 1a (samples A and B) was tested in the propellants HFA 134a (less dense than salmeterol xinafoate) and HFA 227ea (denser), in each case over a 10 minute period. Also tested, under the same conditions, was a sample C of salmeterol xinafoate form I (MMAD 1.1 μm by AEROSIZER™) made by a standard micronization process.

FIG. 1 shows the time variation in flocculation volume of the three samples in HFA 134a, expressed as a percentage of the initial volume. The performance of both SEDS® produced samples (i.e., products according to the present invention) was clearly superior to that of the micronized sample, which after 3 minutes had a flocculation volume below 40% and after 10 minutes of only 30%. The SEDS® samples retained, even after 10 minutes, a flocculation volume of 90% or greater, in the case of sample B greater than 98%.

Sample B was found to retain a flocculation volume of greater than 98% even after 24 hours standing.

The rate of change in flocculation volume for sample A, averaged over the first 2 minutes standing, was −3% per minute. For sample B the rate of change was −0.2% per minute. For the micronized sample C, in contrast, the rate of change was −38% per minute averaged over the first minute. These figures were derived by measuring flocculation volumes during the relevant period and regressing them to a straight line to give an indication of the initial flocculation rate. The error in calculated flocculation rates is approximately 2.5% per minute; thus a flocculation rate of below 2.5% per minute may be equated with negligible sedimentation or creaming.

Figure 2:
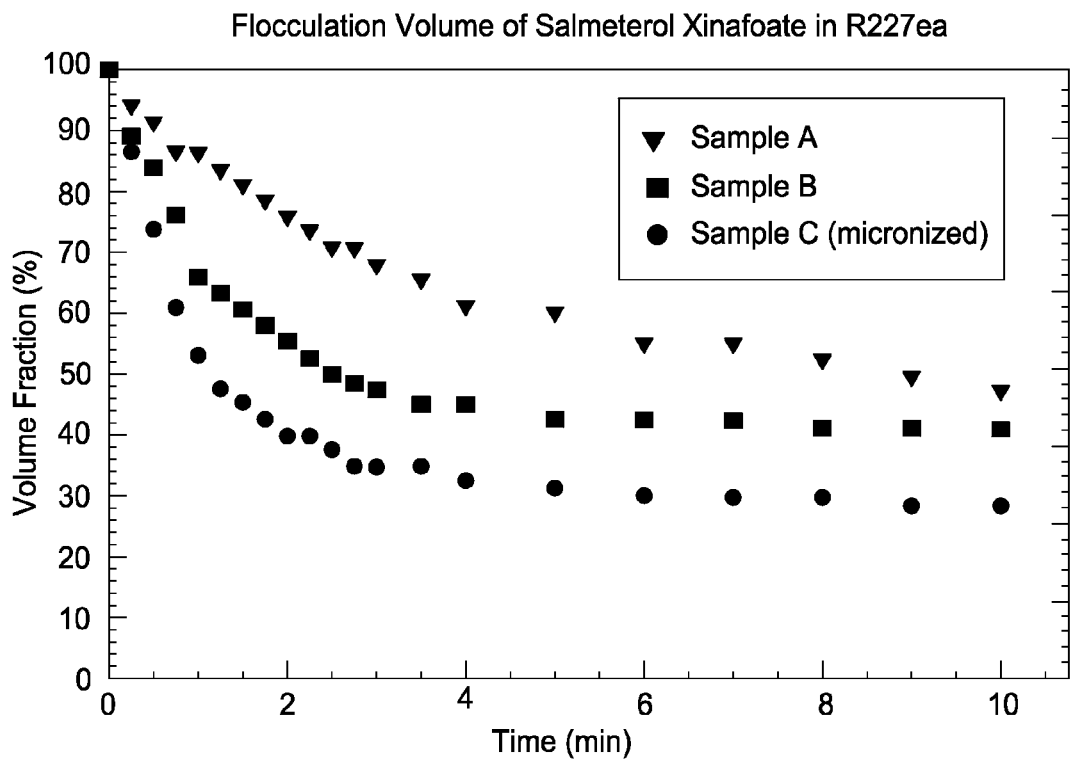

FIG. 2 shows how the same samples performed in HFA 227ea. Again the performance of the SEDS® produced samples A and B was superior to that of the micronized sample C, which after 5 minutes had a flocculation volume below 35%. The SEDS® samples retained a flocculation volume of greater than 40% after 5 and even 10 minutes.

In HFA 227ea, the rates of change in flocculation volume were −11% per minute for sample A and −19% per minute for sample B, both averaged over the first 2 minutes. Sample C exhibited a flocculation rate of −53% per minute over the first minute.

Example 2a

Preparation of Budesonide

Budesonide was precipitated from acetone (2% w/v) at 70° C. and 100 bar. The budesonide solution flow rate was 12.6 mL/min and the $CO_2$ flow rate 833 mL/min. A nozzle with an 800 μm outlet was used. The product MMAD was 1.65 μm (AEROSIZER™).

Example 2b

Flocculation Performance of Budesonide

The flocculation performance of the product of Example 2a was compared, in the propellants HFA 134a (less dense than budesonide) and HFA 227ea (denser), with that of a micronized budesonide sample (MMD 1.5 μm).

Figure 3:
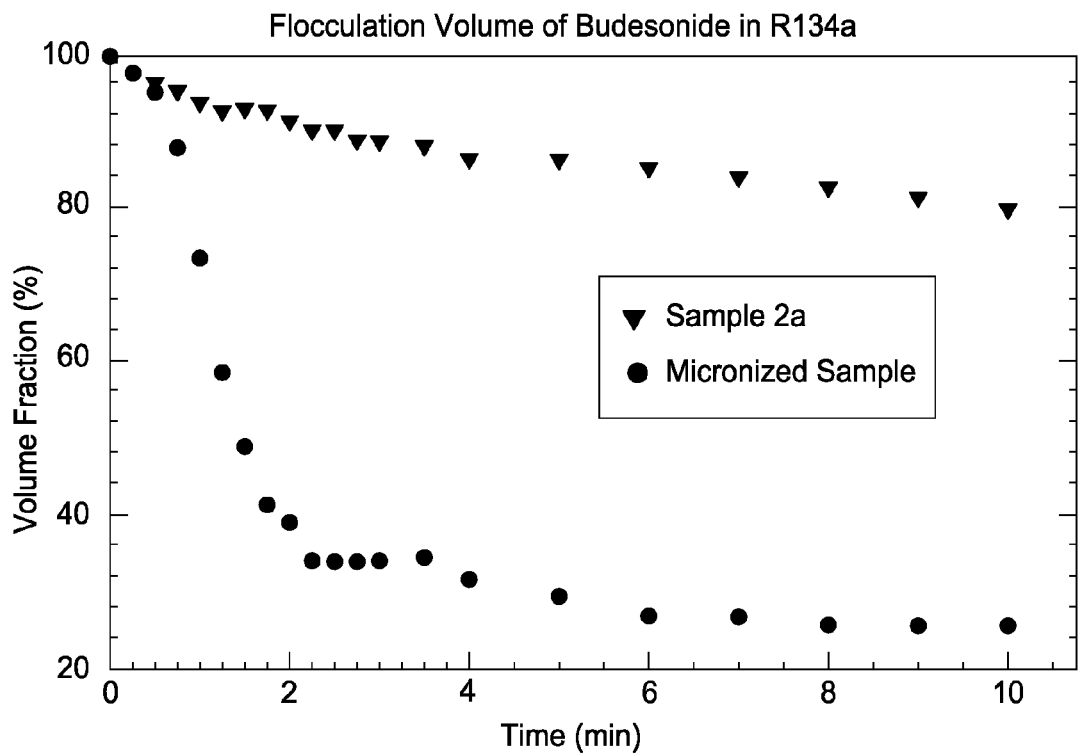

FIG. 3 shows the results in HFA 134a. Again the performance of the product of the invention was significantly better than that of the micronized sample, which after 2 minutes had a flocculation volume below 40% and after 6 minutes of less than 30%. The SEDS® sample, even after 10 minutes, still showed a flocculation volume of 80%. Its rate of change in flocculation volume was −3.5% per minute averaged over the first 2 minutes. The micronized sample exhibited a flocculation rate of −37% per minute over the first minute.

Figure 4:
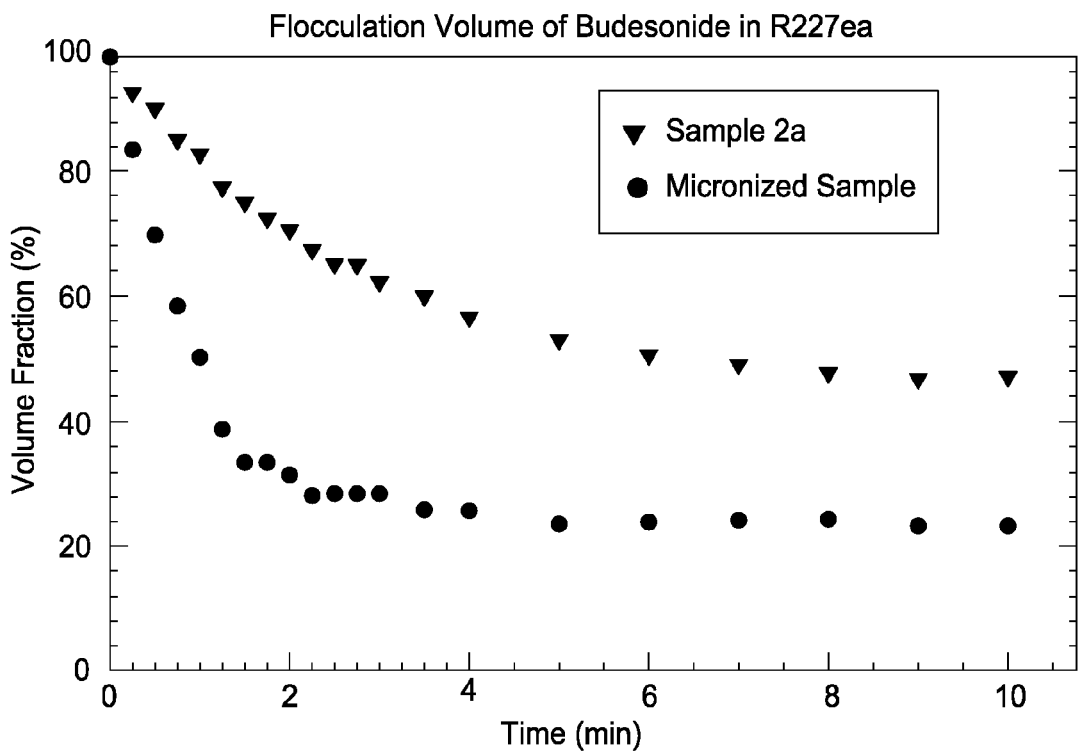

FIG. 4 shows the results in HFA 227ea, demonstrating significantly higher flocculation volumes for the SEDS® sample (greater than 50% after 5 minutes and even after 10 minutes still greater than 40%) as compared to the micronized one. Here the rate of change in flocculation volume for the SEDS® sample was −13% per minute over the first 2 minutes, and for the micronized sample 44% per minute over the first minute.

Example 3a

Preparation of Fluticasone Propionate

Two samples of fluticasone propionate (in two different polymorphic forms I and II) were precipitated from acetone (4% w/v) using the operating conditions set out in Table 1.

TABLE 1

| Sample | Temperature (° C.) | Pressure (bar) | $CO_2$ flow rate (ml/min) | Solution flow rate (ml/min) | Polymorphic form | MMD (μm) (Sympatec ™) |
|---|---|---|---|---|---|---|
| A | 110 | 90 | 20 | 0.3 | I | 2.3 |
| B | 75 | 130 | 25 | 0.5 | II | 5.6 |
| C | 110 | 90 | 20 | 0.3 | I | 2.3 |

Example 3b

Flocculation Performance of Fluticasone Propionate

Samples A and B from Example 3a were compared, in the propellant HFA 134a (less dense than fluticasone propionate), with a micronized sample D of fluticasone propionate form I (MMD 2.0 μm).

Figure 5:
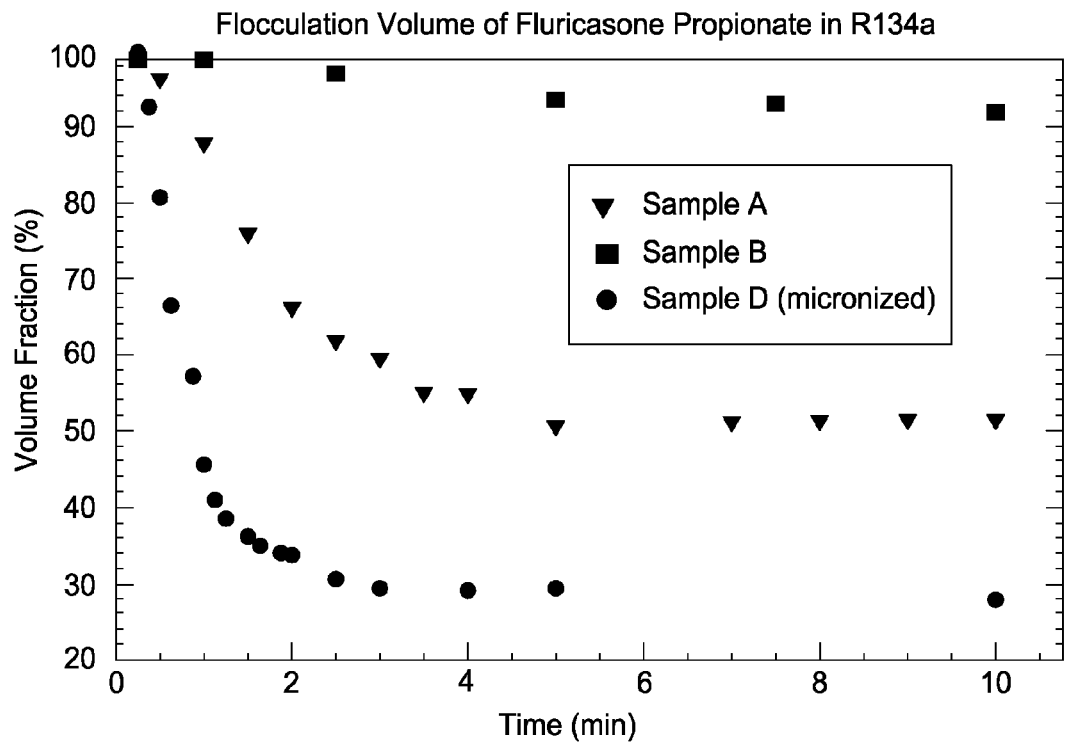

FIG. 5 shows the changes in flocculation volume of the three samples over a 10 minute period, expressed as a percentage of the initial volume. The performance of both SEDS® samples was significantly better than that of the micronized sample D, the latter having a flocculation volume of below 30% after 10 minutes whereas the SEDS® products both retained a flocculation volume of greater than 45% (in the case of the 2.3 μm sample A, about 50%, and in the case of the 5.6 μm sample B, greater than 90%) after the same period.

It is notable that the micronized product, despite being smaller in size than both the SEDS® samples, still does not perform so well in the propellant.

The rates of change in flocculation volume in HFA 134a were −20% per minute for sample A and −1% per minute for sample B, both averaged over the first 2 minutes. Sample D exhibited a flocculation rate of −68% per minute over the first minute.

Figure 6:
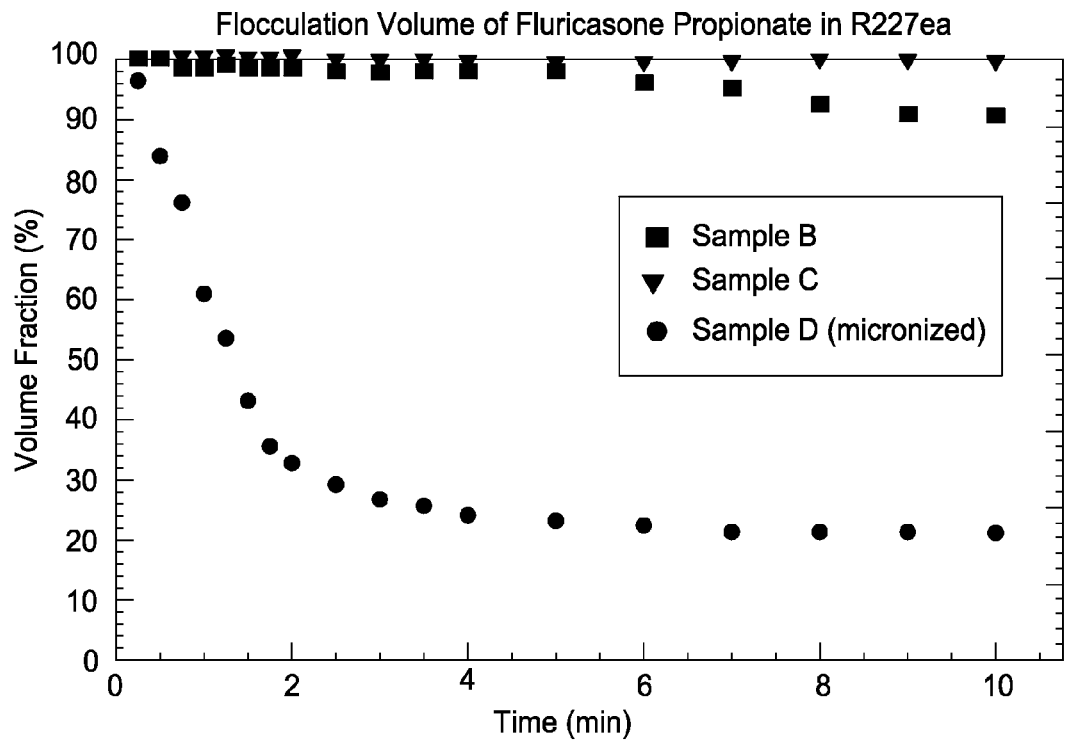

The flocculation behavior of samples B and C from Example 3a was also compared with that of the micronized sample D in the propellant HFA 227ea which is denser than fluticasone propionate. FIG. 6 shows the results. Both SEDS® products exhibited a flocculation volume of greater than 90% even after 10 minutes, sample C performing particularly well, whereas the micronized sample had a flocculation volume of less than 30% after only 3 minutes. The flocculation rates were −0.5% per minute for sample B and 0% per minute for sample C, both averaged over the first 2 minutes. Sample D exhibited a flocculation rate of −40% per minute over the first minute.

Example 4a

Preparation of Salbutamol Sulphate

Salbutamol sulphate was precipitated from methanol (VA w/v), using dichloromethane (DCM) as an anti-solvent modifier. The operating temperature was 75° C., the pressure 200 bar. The salbutamol solution flow rate was 42 mL/min, the DCM flow rate 84 mL/min and the $CO_2$ flow rate 633 mL/min. The nozzle used had a 900 μm diameter outlet.

The product was in the form of plate-like crystals with a MMD of 3.95 μm (SYMPATEC™).

Example 4b

Flocculation Performance of Salbutamol Sulphate

The product of Example 4a was compared, in the propellants HFA 134a (less dense than salbutamol sulphate) and HFA 227ea (denser), with that of a micronized salbutamol sample of MMD 14.5 μm.

Figure 7:
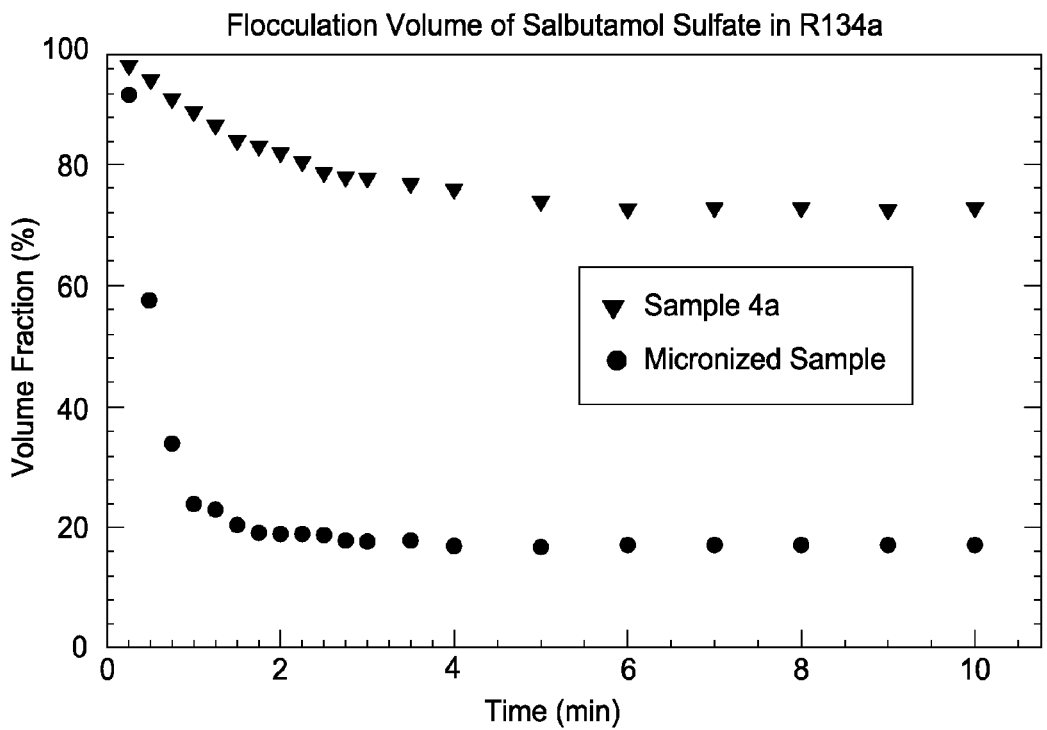

FIG. 7 shows the changes in flocculation volume of the two samples in HFA 134a, over a 10 minute period, expressed as a percentage of the initial volume. The product of the invention performed better than the micronized one, the latter having a flocculation volume of less than 20% after only 2 minutes whereas the SEDS® product retained a flocculation volume greater than 70% over the 10 minute test period. The flocculation rates were −10% per minute for the SEDS® sample, averaged over the first 2 minutes, and −84% per minute for the micronized sample, averaged over the first minute.

Figure 8:
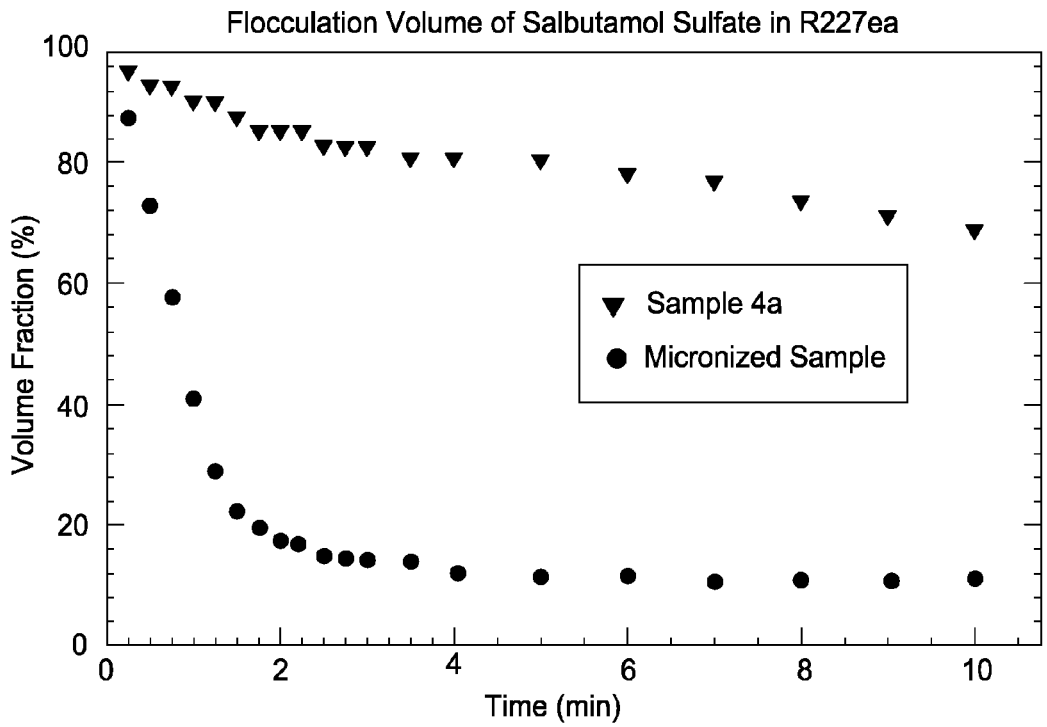
Figure 9:
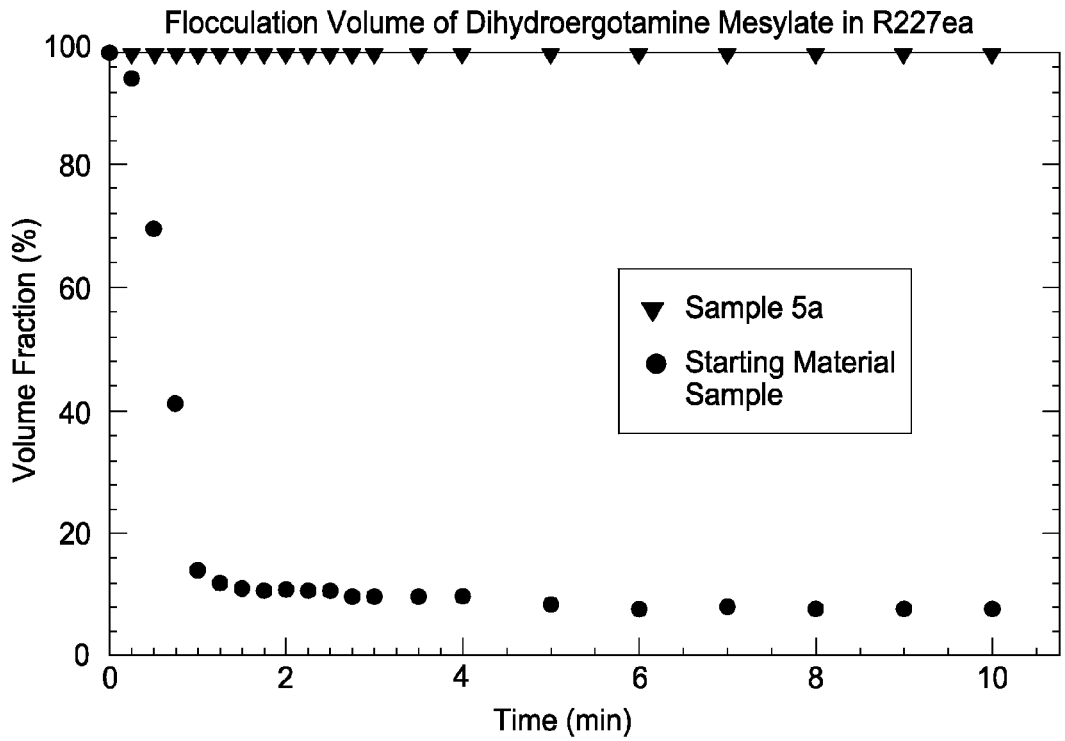
Figure 10:
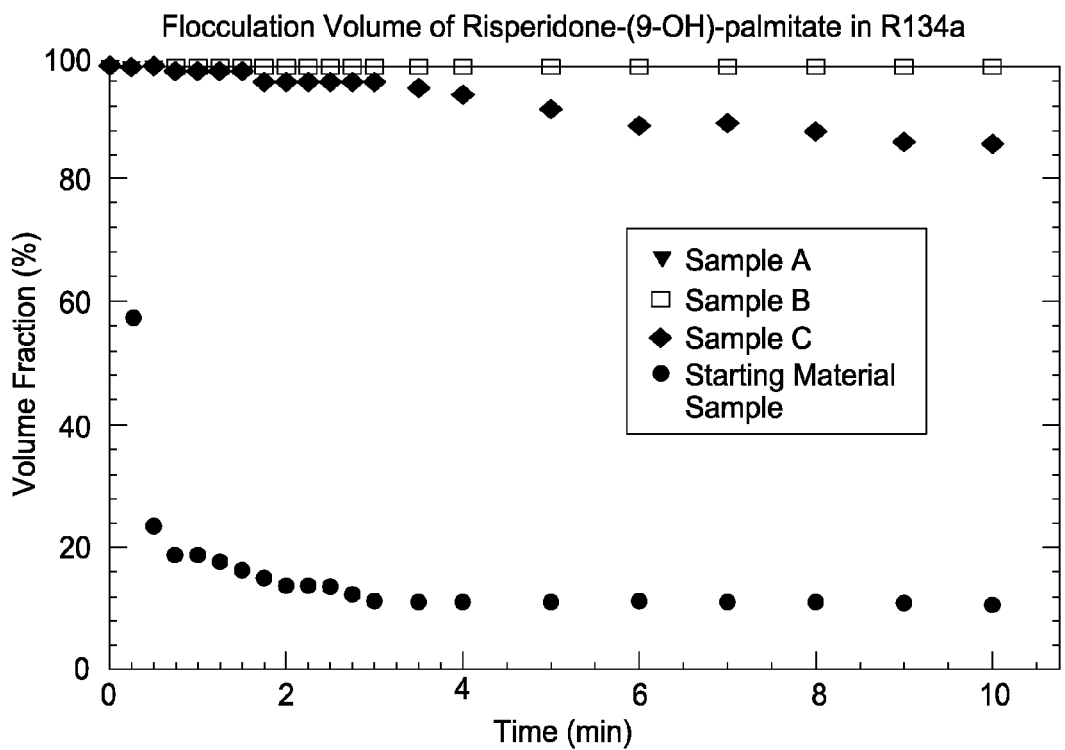
Figure 11:
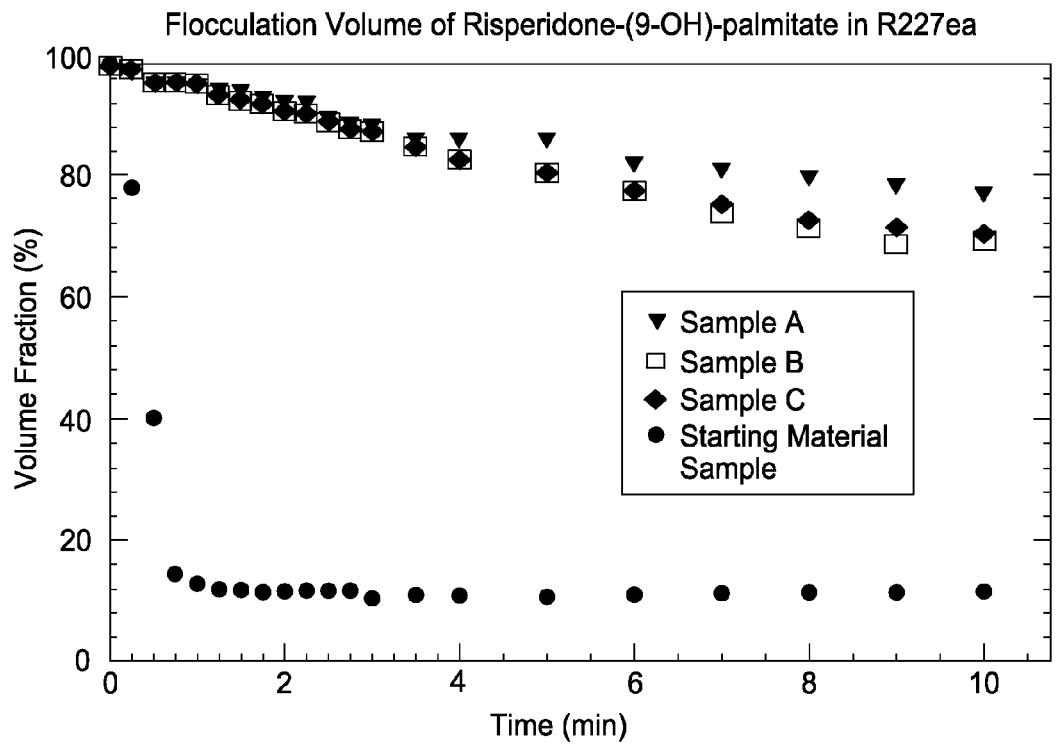
Figure 12:
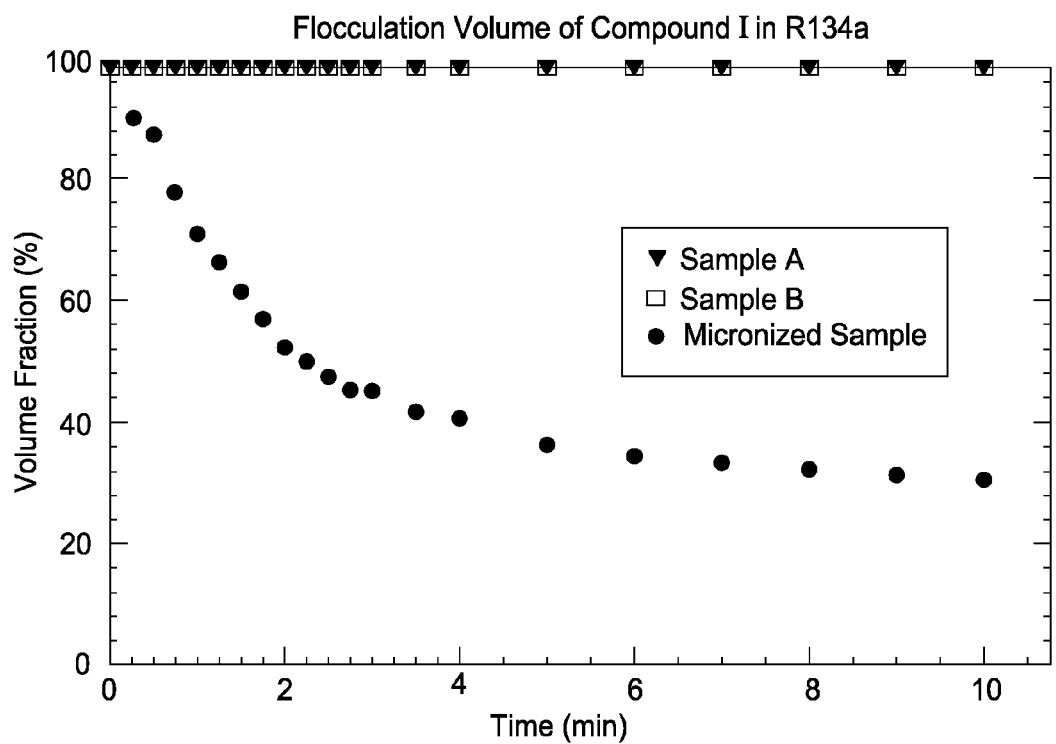
Figure 13:
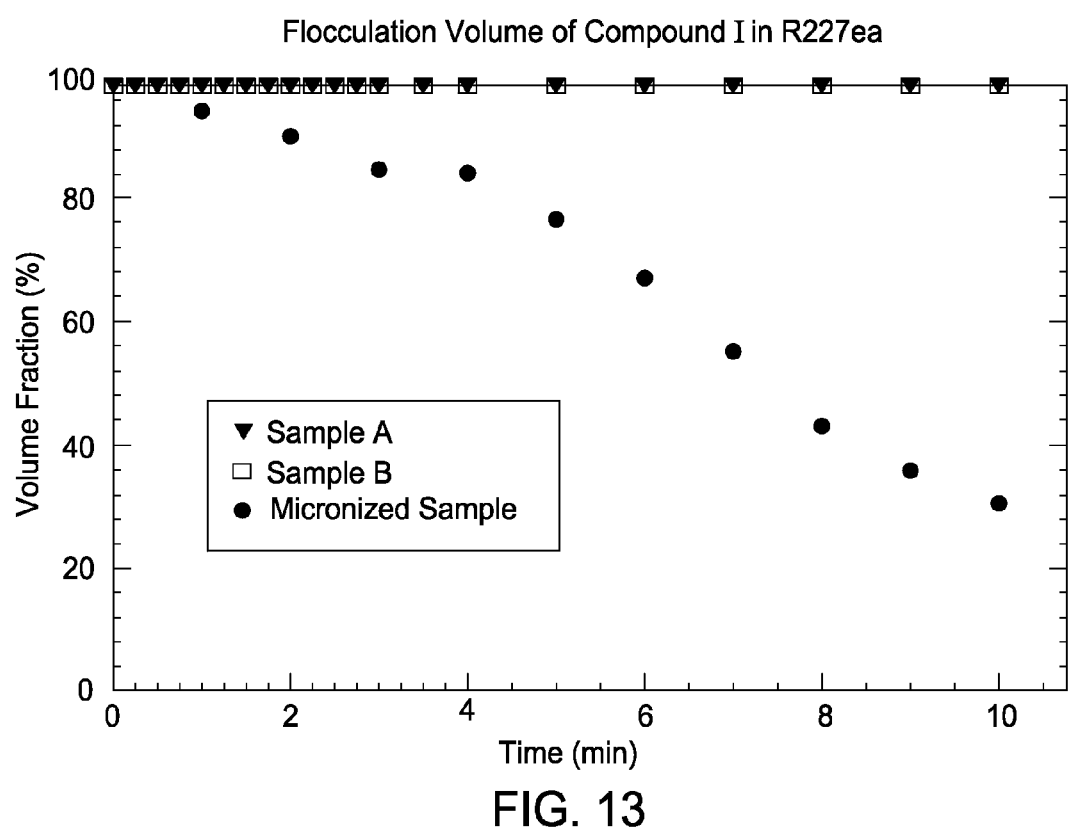

FIG. 8 shows the results in HFA 227ea, in which the micronized sample had a flocculation volume of less than 20% after only 2 minutes whereas the SEDS® product still had a flocculation volume of greater than 70% after 8 minutes and greater than 60% after 10 minutes. The flocculation rates were −5% per minute for the SEDS® sample, averaged over the first 2 minutes, and −55% per minute for the micronized sample, averaged over the first minute.

Example 5a

Preparation of Dihydroergotamine Mesylate

The polar drug dihydroergotamine mesylate (DHE) was precipitated from methanol (5% w/v) at 50° C. and 100 bar. The DHE solution flow rate was 1 mL/min and the $CO_2$ flow rate 200 mL/min. The process used was the modified SEDS® process used for salmeterol sample B in Example 1a, in which the $CO_2$ had a sonic velocity at the nozzle outlet and was pre-heated to 120° C. prior to entering the nozzle. The product had a MMAD of 1.25 µm (AEROSIZER™) and comprised small plate-like crystals.

Example 5b

Flocculation Performance of Dihydroergotamine Mesylate

The flocculation behavior of the product of Example 5a was tested in the propellant HFA 227ea, which is denser than DHE. Also tested was the micronized DHE starting material, which had a MMD of 15.1 μm.

FIG. 9 shows the results for the two samples, the SEDS® product clearly performing better than the micronized version. After 10 minutes, the SEDS® product still exhibited a 100% flocculation volume, whereas after only 1 minute the micronized sample had a flocculation volume of less than 20% and after 5 minutes of less than 10%. Even after 24 hours standing, the SEDS® sample still exhibited no visible creaming in the HFA 227ea.

The flocculation rates were 0% per minute for the SEDS® sample, averaged over the first 2 minutes, and −90% per minute for the micronized sample, averaged over the first minute.

Example 6a

Preparation of Risperidone-(9-hydroxy)-palmitate

The polar drug risperidone-(9-hydroxy)-palmitate was precipitated from tetrahydrofuran (5% w/v) at 80 bar. Two samples A and B were made using a modified SEDS® process as for sample B of Example 1a (sonic velocity $CO_2$; $CO_2$ pre-heated to 90° C.; vessel temperature 36° C.); a third sample C was made using the process as for sample A of Example 1a, using an operating temperature of 41° C. and a nozzle outlet diameter of 400 μm. The risperidone solution flow rate was 4 mL/min for sample A and 1 mL/min for samples B and C. The $CO_2$ flow rate was 200 mL/min in all experiments.

The MMDs (SYMPATEC™) were 2.95 μm for sample A, 2.5 μm for sample B and 3.5 μm for sample C.

Example 6b

Flocculation Performance of Risperidone-(9-hydroxy)-palmitate

The products of Example 6a were compared with the starting material (MMD 8.1 μm) in both HFA 134a and HFA 227ea.

In HFA 134a (FIG. 10), the Example 6a products clearly out-performed the starting material, having in the case of samples A and B a flocculation volume of 100% even after 10 minutes. Sample C still had a flocculation volume of greater than 80% after 10 minutes, compared to the starting material which after only 1 minute had a flocculation volume of less than 20%. The flocculation rates were 0, 0 and −1% per minute for samples A, B and C respectively, averaged over the first 2 minutes, and −152% per minute for the micronized sample, averaged over the first minute.

In HFA 227ea (FIG. 11), all the products of the invention exhibited a flocculation volume of greater than 80% after 5 minutes and greater than 70% after 10 minutes. The starting material, in contrast, again had a flocculation volume of less than 20% after only 1 minute. Here the flocculation rates were −2.5, −3 and −3% per minute for samples A, B and C respectively, averaged over the first 2 minutes, and −117% per minute for the micronized sample, averaged over the first minute.

Example 7a

Preparation of “Compound I”

“Compound I”, an anti-asthma drug, was precipitated from methanol at 80° C. and 200 bar, using a 400 μm outlet nozzle. Two samples A and B were made, using drug solution concentrations of 0.2 and 1.25% w/v respectively. For preparing sample A, the drug solution flow rate was 10 mL/min and the $CO_2$ flow rate 100 mL/min; for sample B the drug solution flow rate was 4.5 mL/min and the $CO_2$ flow rate 150 mL/min. Needle-like crystals were obtained in both cases; their MMDs (SYMPATEC™) were 5.7 and 15.1 μm respectively.

Example 7b

Flocculation Performance of Compound I

The products of Example 7a were compared with a micronized sample of Compound I (MMD 3.4 μm) in both HFA 134a and HFA 227ea.

In HFA 134a (FIG. 12), the Example 7a products both retained a flocculation volume of 100% after 10 minutes, whereas the micronized material had a flocculation volume of less than 35% after the same period. The flocculation rates were 0% per minute for samples A and B, both averaged over the first 2 minutes, and −23% per minute for the micronized sample, averaged over the first minute.

In HFA 227ea (FIG. 13), again the products of the present invention exhibited no creaming during the 10 minute test period, whereas the flocculation volume of the micronized product had fallen to less than 35% by the end of the test. The flocculation rates were again 0% per minute for samples A and B, averaged over the first 2 minutes.

Example 8a

Preparation of Bromocriptine

Bromocriptine mesylate, a polar drug used in the treatment of Parkinson’s disease, was precipitated from ethanol (concentration 1.2% w/v) using a modified SEDS® process as for sample B of Example 1a (sonic velocity $CO_2$; $CO_2$ pre-heated to 90° C.). The operating pressure and temperature were 80 bar and 36° C. respectively. The drug solution flow rate was 1 mL/min for sample A and 4 mL/min for sample B; in both cases the $CO_2$ flow rate was 200 mL/min. The nozzle had a 200 μm outlet diameter.

Sample B precipitated in the form of small plate-like crystals, sample A was amorphous.

Example 8b

Flocculation Performance of Bromocriptine

The flocculation performance of the crystalline product (sample B) of Example 8a was tested in both HFA 134a and HFA 227ea.

In HFA 134a, the sample retained a flocculation volume of 53% after 10 minutes. In HFA 227ea, it still had a flocculation volume of 95% after 10 minutes.

Examples 9

MDI Dosage Uniformity (DHE 0.65% w/w)

Crystalline DHE was prepared by the modified SEDS® process used for salmeterol sample B in Example 1a. The drug was precipitated from a dimethylformamide/water (9:1 v/v) mixture (5% w/v) at 50° C. and 100 bar. The $CO_2$ had a sonic velocity at the nozzle outlet and was pre-heated to 112° C. prior to entering the nozzle. The nozzle had a 0.2 mm outlet diameter and the particle formation vessel a capacity of 2 L. The $CO_2$ flow rate was 12 kg/hour, that for the DHE solution 1 mL/min. The product had the form of thin plate-like particles.

Aerosol formulations were then prepared in accordance with the invention by suspending the DHE in the propellant HFA 134a (DuPont Fluoroproducts, Wilmington, Del.) in 18 mL aluminum pMDI aerosol canisters (Presspart, Cary, N.C.), at a drug concentration of 0.65% w/w. The canisters were equipped with VALOIS™ DF 30/63 RCU 63 µL metering valves (Valois Pharmaceuticals, Marly-le-Roi, France). Note that in all aerosol performance tests, unless otherwise specified, active substance samples were stored, formulated and tested under ambient conditions. Unit doses of these formulations were delivered into an ANDERSEN™ cascade impactor fitted with a USP induction port and operated at 28.3 L/min. Their deposition profiles in the various stages of the impactor, and their MMADs, were measured at the beginning (after priming −5 shots fired to waste) and end of the can life (approximately 100 shots), the aim being to assess the dose uniformity over that period. Standard experimental procedures USP <601> and USP <905> were followed for the cascade impactor and dose content uniformity tests; DHE levels were assessed by HPLC and reported as ex-valve. The interval between shots was at least 30 seconds, to prevent cooling of the aerosol can and consequent moisture condensation.

Each formulation was tested in three aerosol cans. For each can and any given cascade impaction (CI) parameter (e.g., fine particle fraction FPF), a mean value was calculated from the start and end of test values. An overall mean, and the relative standard deviation (RSD) as a percentage of the mean, were also calculated based on all three cans.

The CI measurements and calculated values are shown in Table 2 for (a) the MMAD, (b) the fine particle dose (weight of delivered drug with MMAD <3.3 µm) and (c) the fine particle fraction FPF (percentage of delivered drug particles with MMAD <3.3 µm).

The "% difference" is the difference between the start and end of test values expressed as a percentage of the mean.

TABLE 2

| Aerosol can | Calculation | FPD (µg < 3.3 µm) | FPF (% < 3.3 µm) ex actuator | MMAD (µm) |
|---|---|---|---|---|
| 1 | Mean start/end | 117.8 | 36.4 | 3.11 |
|   | % difference | 8.3 | 11.3 | 9.6 |
| 2 | Mean start/end | 106.6 | 34.8 | 3.22 |
|   | % difference | 0.7 | 9.8 | 4.0 |
| 3 | Mean start/end | 113.9 | 40.4 | 2.69 |
|   | % difference | 0.4 | 12.9 | 1.9 |
| Overall | Mean all 3 cans | 112.8 | 37.2 | 3.00 |
|   | % RSD | 5.3 | 9.4 | 9.1 |

For all three parameters, in particular the fine particle dose, there is good consistency between the start and end of test values, as well as relatively little variation between the three cans. These data indicate good flocculation performance and (from the consistency in MMAD values) low levels of particle growth and aggregation, i.e., stable suspensions of the drug in the propellant. The fine particle fractions and particle sizes make the DHE highly suitable for delivery by inhalation therapy, in particular for systemic delivery via the central lung.

Dose content uniformity was assessed using a Thiel apparatus following the USP method. Again three cans were tested. Measurements for total DHE content in the delivered dose were taken at the start, middle and end of the delivery period, corresponding approximately (after valve priming) to delivered doses 1, 50 and 100. Two priming shots were fired immediately prior to collection of an analytical shot. Mean and % RSD values were calculated across these three measurements, for each can.

The results are shown in Table 3. All measurements (apart from the RSD percentages) are in µg of delivered DHE.

TABLE 3

| Aerosol can | Start | Middle | End | Mean | % RSD |
|---|---|---|---|---|---|
| 4 | 469.80 | 472.26 | 440.62 | 460.89 | 3.82 |
| 5 | 453.98 | 372.45 | 407.79 | 411.41 | 9.94 |
| 6 | 419.26 | 397.08 | 465.15 | 427.16 | 8.13 |

Again, the data show good uniformity in dose content over the test period, indicating good suspension stability.

Examples 10

MDI Dosage Uniformity (DHE 1.3% w/w)

Examples 9 were repeated but formulating the DHE in HFA 134a at a concentration of 1.3% w/w. The results are shown in Tables 4 (CI tests) and 5 (dose content uniformity), and again demonstrate good suspension stability and uniformity of delivery.

TABLE 4

| Aerosol can | Calculation | FPD (µg < 3.3 µm) | FPF (% < 3.3 µm) ex actuator | MMAD (µm) |
|---|---|---|---|---|
| 1 | Mean start/end | 167.9 | 26.1 | 3.595 |
|   | % difference | 0.4 | 6.1 | 4.2 |
| 2 | Mean start/end | 157.0 | 25.2 | 3.64 |
|   | % difference | 21.9 | 30.2 | 7.1 |
| 3 | Mean start/end | 202.9 | 30.95 | 3.51 |
|   | % difference | 13.1 | 26.8 | 5.4 |
| Overall | Mean all 3 cans | 175.9 | 27.4 | 3.58 |
|   | % RSD | 14.5 | 16.5 | 3.6 |

TABLE 5

| Aerosol can | Start | Middle | End | Mean | % RSD |
|---|---|---|---|---|---|
| 4 | 901.11 | 807.10 | 937.99 | 882.07 | 7.65 |
| 5 | 813.66 | 864.35 | 797.93 | 825.31 | 4.21 |
| 6 | 899.94 | 839.24 | 770.06 | 836.42 | 7.77 |

Examples 11

Formulation Stability (DHE)

The stability of aerosol formulations according to the invention was assessed using a thermal cycling treatment designed to simulate a longer term storage period under ambient conditions. Crystalline samples of the drug DHE, prepared as described in Examples 9 (VMD 2.8 µm by SYMPATEC™; bulk powder density 0.14 g/mL), were suspended in HFA 134a in standard pMDI aerosol canisters, as in Examples 9 and 10. Two formulations were prepared, 11A having a DHE concentration of 8 mg/mL and 11B a DHE concentration of 16 mg/mL.

The canisters were subjected to temperature cycling consisting of three 3 or 4 hour cycles between −20° C. and 40° C. for four weeks. Two samples were removed at each of the 1, 2 and 4 week timepoints, and tested for particle size distribution (ANDERSEN™ cascade impaction (ACI), beginning of can life). Dose content uniformity (beginning, middle and end of can life) was assessed at the 1 and 4 week timepoints. The methodology was as in Examples 9. Three samples were also tested pre-thermal cycling (time zero); here particle sizes were assessed at both the beginning and end (100th shot after priming) of the can life to obtain an average MMAD for all 6 measurements.

The particle size (ACI) results are shown in Table 6 for formulation 11A and in Table 7 for formulation 11B. The fine particle fraction FPF is again the fraction having MMAD <3.3 µm.

TABLE 6

| Time point | MMAD (µm) | FPF (%) (actuator + throat + ACI) | FPF (%) (ACI only) | Actuator deposition (%) | Oral dose (%) (throat + 0 + 1) |
|---|---|---|---|---|---|
| 0 | 3.0 | 24.2 | 58.6 | 39.5 | 20.3 |
| 1 week | 3.4 | 22.9 | 47.8 | 35.7 | 18.7 |
| 2 weeks | 3.2 | 24.7 | 52.4 | 34.5 | 20.2 |
| 4 weeks | 3.3 | 24.0 | 50.7 | 32.2 | 22.6 |

TABLE 7

| Time point | MMAD (µm) | FPF (%) (actuator + throat + ACI) | FPF (%) (ACI only) | Actuator deposition (%) | Oral dose (%) (throat + 0 + 1) |
|---|---|---|---|---|---|
| 0 | 3.6 | 18.1 | 39.8 | 37.6 | 20.0 |
| 1 week | 3.6 | 18.3 | 39.5 | 38.7 | 19.2 |
| 2 weeks | 3.6 | 19.5 | 40.0 | 30.0 | 25.4 |
| 4 weeks | 3.6 | 17.9 | 40.5 | 33.1 | 26.0 |

The data in Tables 6 and 7 demonstrate good MMAD and FPF consistency throughout the thermal cycling, indicating a good degree of medium to long term storage stability in the formulations of the invention. Fine particle fractions are high and oro-pharyngeal depositions low.

The dose content uniformity results are shown in Tables 8 and 9 for formulations 11A and 11B respectively. Figures are for DHE dose contents and for the % relative standard deviation (RSD) over the can life.

TABLE 8

| Time point | Dose content (µg) beginning | Dose content (µg) middle | Dose content (µg) end | % RSD |
|---|---|---|---|---|
| 0 | 447.7 | 413.9 | 437.9 | 4.0 |
| 1 week | 513.1 | 496.6 | 464.6 | 5.0 |
| 4 weeks | 436.3 | 444.8 | 463.2 | 3.1 |

TABLE 9

| Time point | Dose content (µg) beginning | Dose content (µg) middle | Dose content (µg) end | % RSD |
|---|---|---|---|---|
| 0 | 871.6 | 836.9 | 835.3 | 2.4 |
| 1 week | 981.8 | 869.2 | 970.5 | 6.6 |
| 4 weeks | 842.3 | 743.0 | 806.0 | 6.3 |

Again these data indicate good formulation stability, dose content uniformity being preserved throughout the thermal cycling.

It is believed that the high crystallinity of the DHE of the invention contributes to its improved stability in aerosol formulations. Amorphous phase regions have a greater tendency to dissolve in a propellant fluid over time, particularly if (as often happens) atmospheric moisture enters the aerosol canister through the valve mechanism. Following this dissolution, the active substance can then re-crystallize around the still suspended particles, leading to particle growth and/or aggregation and a resultant change in the MMAD as well as in the ultimate aerosol performance. The DHE formulations of the invention appear to have a high degree of stability in this respect, even under conditions representing extended storage periods.

Examples 12

MDI Delivery Efficiency (Bromocriptine)

Amorphous and crystalline bromocriptine mesylate samples were prepared as described in Example 8a. Again sample A was amorphous and sample B highly crystalline.

Aerosol formulations 12A and 12B, containing the bromocriptine samples A and B respectively suspended in HFA 227ea, were prepared in 19 mL aluminum aerosol canisters (Presspart Inc., Cary, N.C.) equipped with 50 µL metering valves (Valois Pharmaceuticals, Marly-le-Roi, France). The suspension concentrations were 0.7% w/w for formulation 12A and 0.69% w/w for 12B. A control formulation 12C was prepared containing 0.74% w/w micronized bromocriptine. In each case the powder was dispersed in the propellant by first sonicating the canisters for 10-15 seconds in a bath sonicator and then placing them on a wrist-action shaker for about 30 minutes. Each canister was then primed by wasting the first 5 shots.

The formulations were tested on an ANDERSEN™ cascade impactor to determine their aerodynamic particle properties. The cascade impactor was operated at 28.3 L/min and fitted with a USP induction port (<USP 601> Pharmacopeial Previews 22, 3065 (1995)). The particle size distributions were fractionated into mass of drug deposited on the pMDI actuator, USP induction port, eight stages and terminal filter. Five shots were actuated per test, with an interval of at least 30 seconds between shots to prevent cooling of the can and resultant moisture condensation. The bromocriptine content in each sample was determined by HPLC. The percentage of the total dose deposited from stage 4 to the terminal filter (corresponding to particles of MMAD less than 3.3 µm) was considered to be the fine particle fraction.

Measurements were recorded across (a) 5 shots delivered at the start of the experiment, after priming, (b) 5 shots in the middle of the experiment and (c) 5 shots towards the end of the canister (total number of shots per experiment approximately 120).

The tests for each of formulations 12A to 12C were conducted in triplicate, using three separate aerosol cans. A mean value was calculated for each parameter, based on the nine measurements obtained (i.e., start, middle and end of test values for each of the three cans), together with the standard deviation SD.

The results are shown in Table 10. FPD is the fine particle dose and FPF the fine particle fraction.

TABLE 10

| Sample | | FPD (μg < 3.3 μm) | FPF (% < 3.3 μm) | MMAD (μm) |
|---|---|---|---|---|
| 12A | Mean | 180.48 | 38.41 | 3.26 |
|  | SD | 11.16 | 1.97 | 0.10 |
| 12B | Mean | 128.80 | 27.41 | 3.76 |
|  | SD | 9.60 | 1.47 | 0.06 |
| 12C | Mean | 104.17 | 21.84 | 3.89 |
|  | SD | 9.79 | 0.91 | 0.07 |

Generally speaking, in the tests involving formulations 12A and 12B according to the invention, extremely low variations (SD<3 for the FPF, and <0.2 for the MMAD) were seen between the start, middle and end of test values recorded for each of the three cans. Overall, consistently good performance was observed for the formulations of the invention, which yielded fine aerosols with higher fine particle fractions and decreased throat deposition as compared to the micronized control.

Examples 13

MDI Dosage Uniformity (Bromocriptine)

Dose content uniformity for the three formulations 12A to 12C, over the entire contents of the filled aerosol canisters, was further confirmed by subjecting them to a test protocol analogous to that used in Examples 9. Using a baseplate (quadrapod) apparatus, from a 0.6 mm outside diameter Valois boot actuator (Valois Pharmaceuticals, Marly-le-Roi, France), each formulation was actuated and collected into 10 mL of methanol/water. The bromocriptine content of each delivered dose was determined in duplicate at the beginning, middle and end of each filled canister, by HPLC analysis.

Table 11 shows the mean dose contents across three aerosol cans for each formulation, determined at the start, middle and end of the can life. Also shown is the overall mean dose content for each formulation, together with the calculated % RSD which gives an indication of the variation in dose content through the can life. Again all measurements (apart from the RSD percentages) are in μL of delivered drug.

TABLE 11

| Formulation | | Start | Middle | End | Overall average |
|---|---|---|---|---|---|
| 12A | Mean dose (μg) | 604.31 | 591.80 | 591.71 | 595.94 |
|  | % RSD | 2.28 | 2.37 | 3.64 | 2.84 |
| 12B | Mean dose (μg) | 623.58 | 615.87 | 723.30 | 654.25 |
|  | % RSD | 4.62 | 7.10 | 12.66 | 11.65 |
| 12C | Mean dose (μg) | 662.02 | 612.65 | 672.53 | 649.07 |
|  | % RSD | 16.47 | 27.49 | 12.95 | 18.74 |

Again, the data for formulations 12A and 12B show good uniformity in dose content over the test period, in particular compared to formulation 12C containing the micronized drug. This indicates good suspension stability for the formulations according to the invention. Even where the active substance is present in the amorphous phase, it appears to have extremely good suspension stability in HFA 227ea, which in turn indicates improved stability against re-crystallization—this is thought to be due to increased purity, and in particular to reduced residual solvent levels, when an active substance is prepared in accordance with the invention as opposed to by a conventional route such as crystallization followed by micronization.

The invention claimed is:

1. Particles of an active substance, wherein the particles are non-micronized, solid, have a mass median aerodynamic diameter of less than 10 μm, and exhibit a flocculation volume of about 85% or greater about 1 minute after mixing the particles with a nonsolvent hydrofluorocarbon fluid vehicle at a concentration within a range from about 0.2% w/v to about 5% w/v,
wherein the active substance comprises an ergot alkaloid, pharmaceutically acceptable salts thereof, analogues thereof, or derivatives thereof.

2. The particles of claim 1, wherein the ergot alkaloid comprises dihydroergotamine, pharmaceutically acceptable salts thereof, analogues thereof, or derivatives thereof.

3. The particles of claim 2, wherein the ergot alkaloid is dihydroergotamine mesylate.

4. The particles of claim 1, wherein the hydrofluorocarbon fluid vehicle comprises 1,1,1,2-tetrafluoroethane (HFA 134a), 1,1,1,2,3,3,3-heptafluoropropane (HFA 227ea), or mixtures thereof.

5. The particles of claim 1, wherein the particles exhibit a flocculation volume of about 85% or greater about 5 minutes after mixing the particles and the hydrofluorocarbon fluid vehicle.

6. The particles of claim 5, wherein the particles exhibit a flocculation volume of about 85% or greater about 10 minutes after mixing the particles and the hydrofluorocarbon fluid vehicle.

7. The particles of claim 6, wherein the particles exhibit a flocculation volume of about 100% about 10 minutes after mixing the particles and the hydrofluorocarbon fluid vehicle.

8. The particles of claim 1, wherein the particles are mixed with the hydrofluorocarbon fluid vehicle at a concentration within a range from about 0.2% w/v to about 3% w/v.

9. The particles of claim 8, wherein the particles are mixed with the hydrofluorocarbon fluid vehicle at a concentration within a range from about 0.5% w/v to about 1.5% w/v.

10. The particles of claim 1, wherein the mass median aerodynamic diameter of the particles is about 5 μm or less.

11. The particles of claim 10, wherein the mass median aerodynamic diameter of the particles is about 3 μm or less.

12. The particles of claim 1, wherein the active substance is in a crystalline form.

13. Particles of an active substance, wherein the particles are non-micronized, solid, have a mass median aerodynamic diameter of less than 15 μm, and exhibit a flocculation volume of about 35% or greater about 1 minute after mixing the particles with a nonsolvent hydrofluorocarbon fluid vehicle at a concentration within a range from about 0.2% w/v to about 5% w/v,
wherein the active substance comprises an ergot alkaloid, pharmaceutically acceptable salts thereof, analogues thereof, or derivatives thereof.

14. The particles of claim 13, wherein the ergot alkaloid comprises dihydroergotamine, pharmaceutically acceptable salts thereof, analogues thereof, or derivatives thereof.

15. The composition of claim 14, wherein the ergot alkaloid is dihydroergotamine mesylate.

16. The particles of claim 13, wherein the hydrofluorocarbon fluid vehicle comprises 1,1,1,2-tetrafluoroethane (HFA 134a), 1,1,1,2,3,3,3-heptafluoropropane (HFA 227ea), or mixtures thereof.

17. The particles of claim 16, wherein the mass median diameter of the particles is about 10 μm or less.

18. The particles of claim 17, wherein the mass median diameter of the particles is about 5 μm or less.

19. The particles of claim 13, wherein the particles exhibit a flocculation volume of about 85% or greater about 10 minutes after mixing the particulate active substance and the hydrofluorocarbon fluid vehicle.

20. The particles of claim 13, wherein the particles are mixed with the hydrofluorocarbon fluid vehicle at a concentration within a range from about 0.2% w/v to about 3% w/v.

* * * * *

UNITED STATES PATENT AND TRADEMARK OFFICE
CERTIFICATE OF CORRECTION

PATENT NO. : 8,828,359 B2
APPLICATION NO. : 13/908540
DATED : September 9, 2014
INVENTOR(S) : Kordikowski et al.

It is certified that error appears in the above-identified patent and that said Letters Patent is hereby corrected as shown below:

In the Specification

Column 9, Line 18, please delete "(e.g.,(3- or γ-interferon)" and insert -- (e.g., β- or γ-interferon) -- therefor;

Column 9, Line 30, please delete "Vila" and insert -- VIIa -- therefor;

Column 24, Line 12, please delete "(VA w/v)" and insert -- (1% w/v) -- therefor.

Signed and Sealed this
Twenty-fourth Day of February, 2015

Michelle K. Lee
*Deputy Director of the United States Patent and Trademark Office*